(12) United States Patent
Shimuta et al.

(10) Patent No.: US 11,656,132 B2
(45) Date of Patent: May 23, 2023

(54) STICKING TYPE THERMOMETER

(71) Applicant: Murata Manufacturing Co., Ltd., Nagaokakyo (JP)

(72) Inventors: Toru Shimuta, Nagaokakyo (JP); Yoshihide Amagai, Nagaokakyo (JP)

(73) Assignee: MURATA MANUFACTURING CO, LTD., Nagaokakyo (JP)

( * ) Notice: Subject to any disclaimer, the term of this patent is extended or adjusted under 35 U.S.C. 154(b) by 205 days.

(21) Appl. No.: 16/902,542

(22) Filed: Jun. 16, 2020

(65) Prior Publication Data

US 2020/0309608 A1 Oct. 1, 2020

Related U.S. Application Data

(63) Continuation of application No. PCT/JP2018/046048, filed on Dec. 14, 2018.

(30) Foreign Application Priority Data

Dec. 27, 2017 (JP) .............................. JP2017-250409
Apr. 26, 2018 (JP) .............................. JP2018-084802

(51) Int. Cl.
*G01K 13/20* (2021.01)
*A61B 5/00* (2006.01)
(Continued)

(52) U.S. Cl.
CPC ............ *G01K 13/20* (2021.01); *A61B 5/6801* (2013.01); *A61B 5/683* (2013.01); *A61B 5/6832* (2013.01);
(Continued)

(58) Field of Classification Search
CPC ............ G01K 13/20; G01K 1/14; G01K 7/16; G01K 7/18; A61B 5/6801; A61B 5/683;
(Continued)

(56) References Cited

U.S. PATENT DOCUMENTS

| 6,649,994 B2 * | 11/2003 | Parsons | .................. | H01C 7/022 |
| | | | | 374/E7.018 |
| 6,765,278 B2 * | 7/2004 | Parsons | .................. | H01C 7/022 |
| | | | | 374/E7.018 |

(Continued)

FOREIGN PATENT DOCUMENTS

| JP | 2001314378 A | 11/2001 |
| JP | 2003270051 A | 9/2003 |

(Continued)

OTHER PUBLICATIONS

International Search Report issued for PCT/JP2018/046048, dated Jan. 15, 2019.

(Continued)

*Primary Examiner* — Nathaniel T Woodward
*Assistant Examiner* — Philip L Cotey
(74) *Attorney, Agent, or Firm* — ArentFox Schiff LLP

(57) ABSTRACT

A sticking type deep-body thermometer is provided that includes a body temperature measurement unit having a wiring substrate on which four temperature sensors and a processing circuit are mounted. The thermometer includes an upper case accommodating the body temperature measurement unit, a lower case that is in close contact with the upper case and a peripheral edge portion, and a sticking member stuck to an outer side surface of the lower case. The sticking member is formed in a sheet-like shape, has a pair of sticking surfaces with adhesiveness, and one sticking surface of the pair of sticking surfaces is stuck to the outer side surface of the lower case in a peelable manner.

19 Claims, 22 Drawing Sheets

(51) Int. Cl.
    *G01K 1/14*     (2021.01)
    *G01K 7/18*     (2006.01)
    *G01K 7/16*     (2006.01)
    *A61B 5/01*     (2006.01)

(52) U.S. Cl.
    CPC ........ *A61B 5/6833* (2013.01); *A61B 5/68335* (2017.08); *G01K 1/14* (2013.01); *G01K 7/16* (2013.01); *G01K 7/18* (2013.01); *A61B 5/0008* (2013.01); *A61B 5/01* (2013.01); *A61B 5/68* (2013.01)

(58) Field of Classification Search
    CPC . A61B 5/6832; A61B 5/6833; A61B 5/68335; A61B 5/0008; A61B 5/01; A61B 5/68
    See application file for complete search history.

(56) References Cited

U.S. PATENT DOCUMENTS

| | | | | |
|---|---|---|---|---|
| 6,989,574 B2* | 1/2006 | Parsons | ................ | G01K 7/16 |
| | | | | 374/E7.018 |
| 7,354,195 B2* | 4/2008 | Sakano | ................ | G01K 1/024 |
| | | | | 374/E1.004 |
| 8,790,384 B2* | 7/2014 | Uchiyama | ........... | A61F 13/0206 |
| | | | | 607/112 |
| 9,183,738 B1* | 11/2015 | Allen, Sr | ............... | G01K 13/20 |
| 2002/0179992 A1* | 12/2002 | Parsons | ................ | H01C 7/022 |
| | | | | 257/469 |
| 2003/0146502 A1* | 8/2003 | Parsons | ................ | H01C 7/022 |
| | | | | 374/E7.018 |
| 2004/0169249 A1* | 9/2004 | Parsons | ................ | H01C 7/022 |
| | | | | 374/E7.018 |
| 2004/0242976 A1* | 12/2004 | Abreu | ................ | A61B 5/746 |
| | | | | 600/315 |
| 2005/0101843 A1* | 5/2005 | Quinn | ................ | G01K 1/024 |
| | | | | 374/E1.004 |
| 2005/0141591 A1* | 6/2005 | Sakano | ................ | G01K 15/00 |
| | | | | 374/E1.004 |
| 2006/0019069 A1* | 1/2006 | Ikishima | ................ | C09J 7/38 |
| | | | | 428/156 |
| 2009/0102611 A1* | 4/2009 | Quinn | ................ | G01K 1/024 |
| | | | | 340/10.3 |
| 2011/0218601 A1* | 9/2011 | Uchiyama | ........... | A61F 13/0259 |
| | | | | 607/112 |
| 2012/0238901 A1* | 9/2012 | Augustine | ................ | A61B 5/01 |
| | | | | 600/549 |
| 2013/0101819 A1* | 4/2013 | Suzuki | ............... | C08F 220/1804 |
| | | | | 428/337 |
| 2016/0183794 A1* | 6/2016 | Gannon | ................ | G01K 1/024 |
| | | | | 600/549 |
| 2017/0238812 A1* | 8/2017 | Atlas | .................... | A61B 5/1117 |
| 2019/0046033 A1* | 2/2019 | Gannon | ................ | G01K 1/024 |
| 2020/0278260 A1* | 9/2020 | Shimuta | ................ | G01K 13/20 |

FOREIGN PATENT DOCUMENTS

| | | |
|---|---|---|
| JP | 2004507728 A | 3/2004 |
| JP | 2007512865 A | 5/2007 |
| JP | 2011182876 A | 9/2011 |
| JP | 2012154859 A | 8/2012 |
| JP | 2013044625 A | 3/2013 |
| JP | 2015111048 A | 6/2015 |
| JP | 2016049753 A | 4/2016 |
| WO | 03024568 A2 | 3/2003 |
| WO | 03024568 A3 | 7/2003 |
| WO | 2013024568 A1 | 2/2013 |

OTHER PUBLICATIONS

Written Opinion of the International Searching Authority issued for PCT/JP2018/046048, dated Jan. 15, 2019.

* cited by examiner

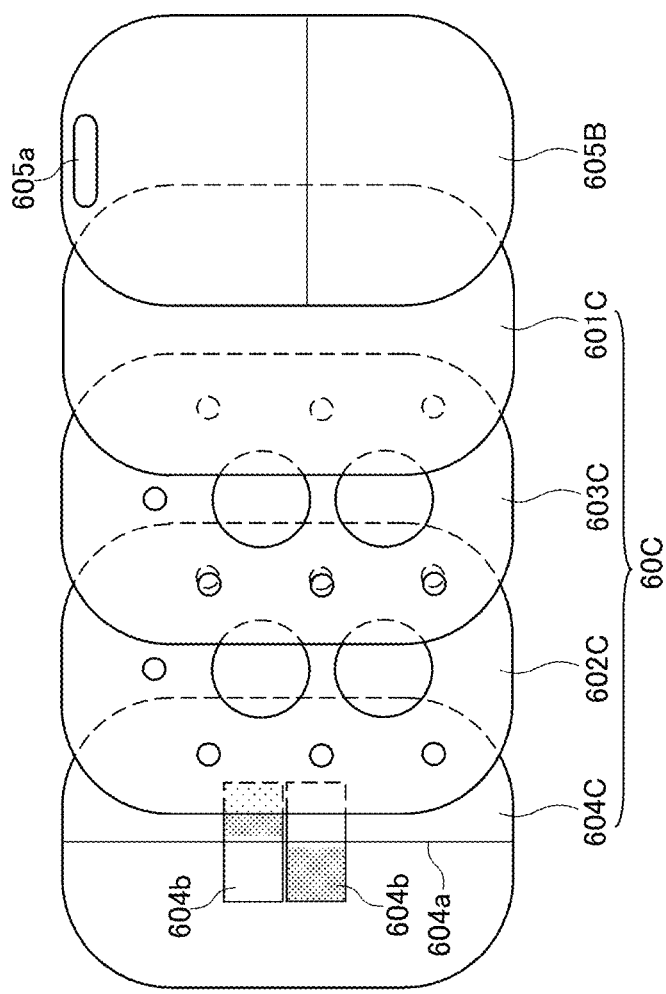
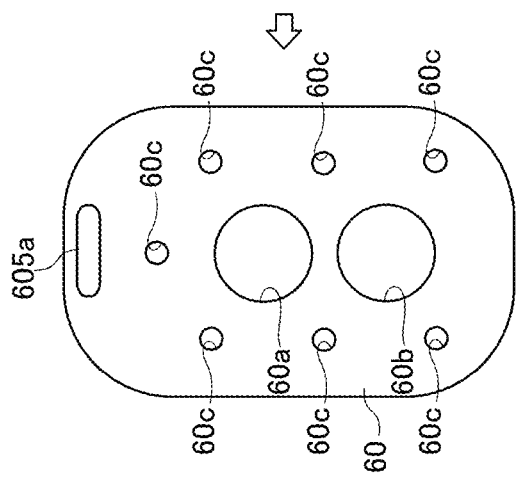
FIG. 14

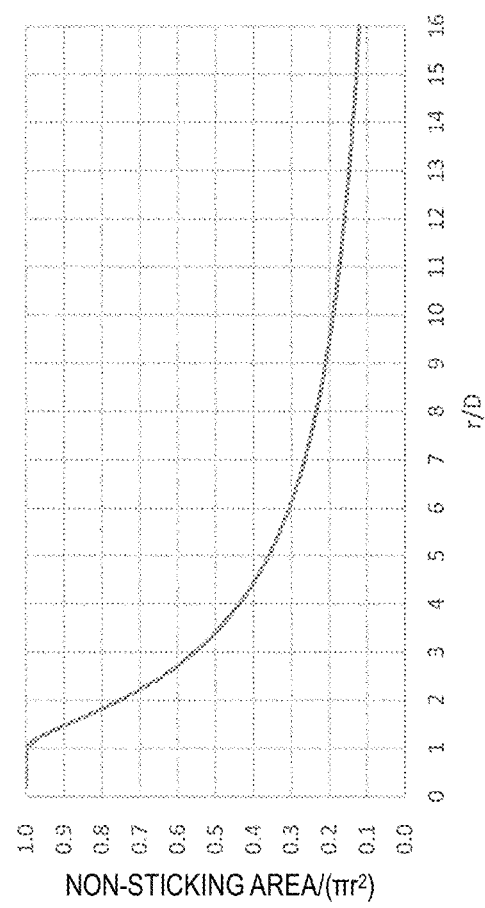

STICKING TYPE THERMOMETER

CROSS REFERENCE TO RELATED APPLICATIONS

The present application is a continuation of PCT/JP2018/046048 filed Dec. 14, 2018, which claims priority to Japanese Patent Application No. 2018-084802, filed Apr. 26, 2018, and to Japanese Patent Application No. 2017-250409, filed Dec. 27, 2017, the entire contents of each of which are incorporated herein by reference.

TECHNICAL FIELD

The present invention relates to a sticking type thermometer for measuring a body temperature, and particularly, to a sticking type thermometer that is stuck to a body surface and acquires body temperature data by continuously measuring the body temperature.

BACKGROUND

In the past, there has been a thermometer that can be stuck to a body surface, continuously measure a body temperature, and acquire body temperature data. For example, Patent Document 1 (identified below) discloses a non-heating type thermometer that is stuck to a body surface of a subject and measures a deep-body temperature of the subject.

More specifically, the thermometer includes first and second thermal resistors in which a first temperature sensor is disposed on one side surface in contact with a body surface and a second temperature sensor is disposed on the other side surface facing the one side surface. Moreover, a uniform member is provided to cover only the other side surfaces of the first and second thermal resistors, a heat insulation member is disposed to surround the side surfaces of the first and second thermal resistors, and a protection member is provided whose peripheral edge portion is fixed to the other side surface of the heat insulation member and whose central portion is disposed with a predetermined space from the uniforming member. Further, the entire body surface side of the thermometer is covered by a sticking tape, such as adhesive layer.

Patent Document 1: Japanese Unexamined Patent Application Publication No. 2012-154859.

As described above, according to the thermometer described in Patent Document 1, since the entire body surface side of the thermometer is covered by a sticking tape, the thermometer can be easily attached to the body surface of a subject. However, when the thermometer is repeatedly used, the adhesive strength of the sticking tape decreases, close contact to the body surface decreases, and there is a risk that the measurement accuracy of the body temperature decreases.

On the other hand, in a case of a disposable type which is disposed each time a thermometer is used, the cost increases. Whereas, in the thermometer described in Patent Document 1, a point that the thermometer is repeatedly used without increasing the cost and without decreasing the measurement accuracy is not considered at all.

SUMMARY OF THE INVENTION

The present invention has been made in order to solve the above-described problem. Accordingly, it is an object of the present invention to provide a sticking type thermometer that is stuck to a body surface and continuously measures a body temperature to acquire body temperature data and also to provide a sticking type thermometer configured to be repeatedly used without increasing the cost and without decreasing the measurement accuracy.

According to an exemplary embodiment, a sticking type thermometer is provided that is configured to be stuck to a body surface and to continuously measure a body temperature to acquire body temperature data. The thermometer includes a body temperature measurement unit including a temperature detector, a wiring substrate on which a processing circuit to process an output signal of the temperature detector, an upper case accommodating the body temperature measurement unit, a lower case in close contact with the upper case, and a sticking member stuck to the outer side surface of the lower case. The sticking member is formed as a sheet-like shape, has a pair of sticking surfaces with adhesiveness, and the one sticking surface of the pair of sticking surfaces is stuck to the outer side surface of the lower case in a peelable manner.

According to the sticking type thermometer of the exemplary embodiment, the sticking member is formed as a sheet-like shape, has a pair of sticking surfaces with adhesiveness, and one sticking surface of the pair of sticking surfaces is stuck to the outer side surface of the lower case in the peelable manner. Therefore, it is possible to peel off the used sticking member from the lower case after use (e.g., after acquisition of body temperature) and stick a new sticking member to the lower case. That is, it is possible to repeatedly use a main body portion that includes the body temperature measurement unit, the upper case, and the lower case by replacing with a new sticking member. Further, since the sticking member for sticking the sticking type thermometer to the body surface is replaced, it is possible to prevent the sticking type thermometer from being decreased in the measurement accuracy due to a decrease in adhesive strength or the like. As the result, it is further possible to repeatedly use without increasing the cost and without decreasing the measurement accuracy.

According to the exemplary embodiment, a sticking type thermometer is provided that is configured to be stuck to a body surface, configured to continuously measure the body temperature and acquire the body temperature data. Moreover, the thermometer can be repeatedly used without increasing the cost and without decreasing the measurement accuracy.

BRIEF DESCRIPTION OF DRAWINGS

FIG. 14 is a plan view and an exploded view illustrating a sticking member forming the deep-body thermometer according to the fourth modification of an exemplary embodiment.

FIG. 17 is a graph illustrating a relationship between a ratio (r/D) where r/D is a ratio of the radius r of the through-hole and a non-sticking area, to the thickness D of the ventilation layer and the second sticking layer.

DETAILED DESCRIPTION OF EMBODIMENTS

Figure 1:
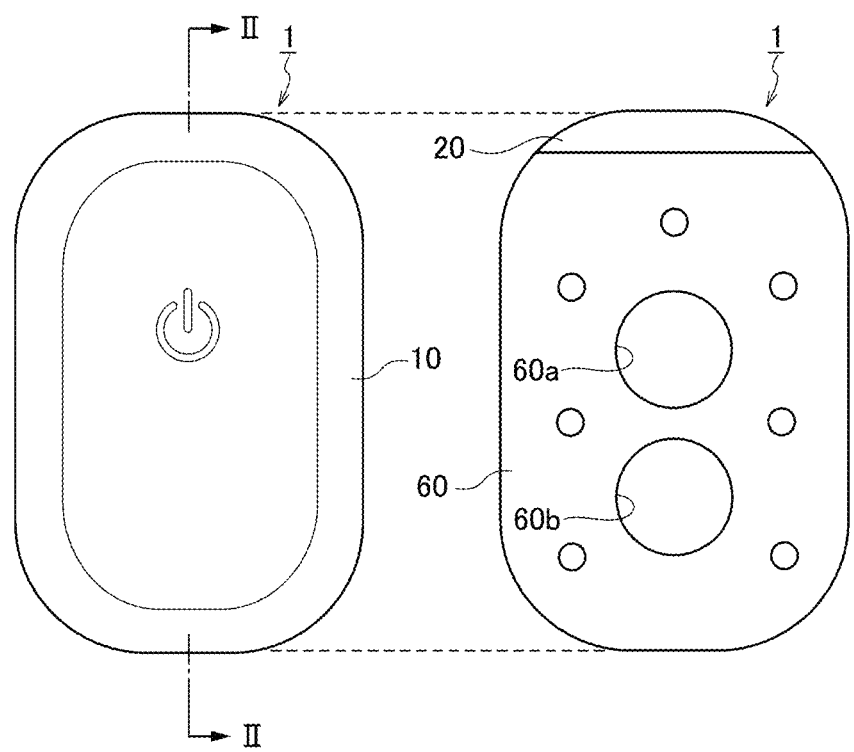
FIG. 1 is a plan view and a bottom view illustrating an appearance of a deep-body thermometer according to an exemplary embodiment.

Hereinafter, exemplary embodiments of the present invention will be described in detail with reference to the accompanying drawings. In the drawings, the same or corresponding portions will be denoted by the same reference numerals. In each drawing, the same elements are denoted by the same reference numerals, and repeated description thereof will be omitted.

Figure 2:
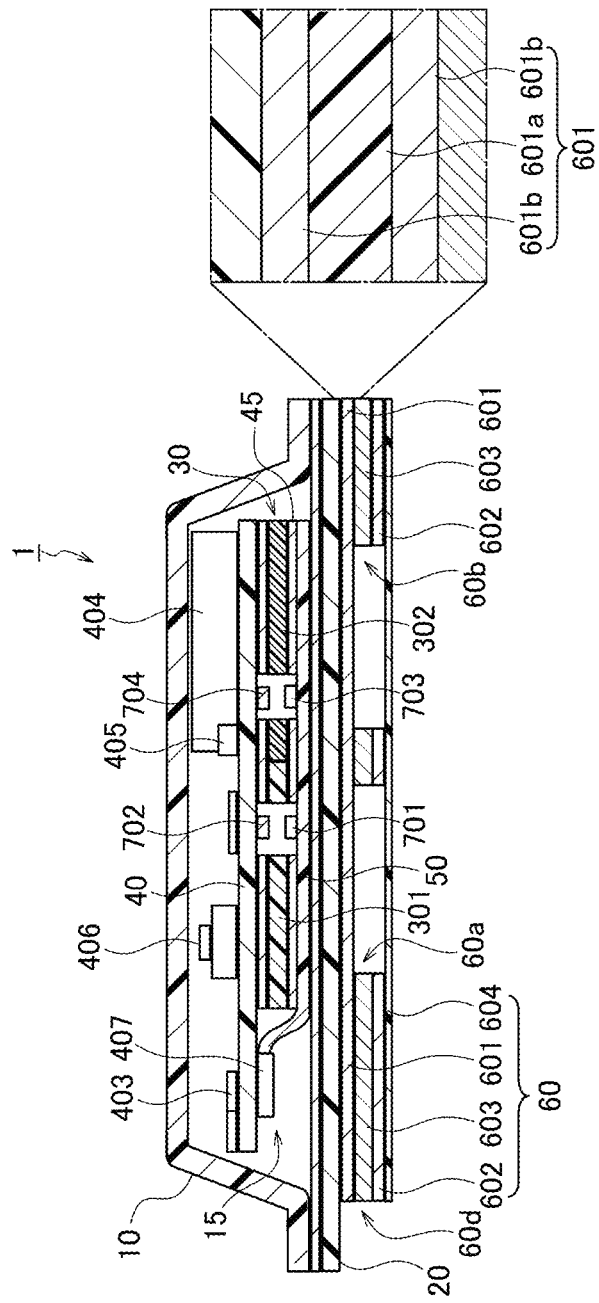
FIG. 2 is a cross-sectional view illustrating a configuration of the deep-body thermometer according to the exemplary embodiment.
Figure 3:
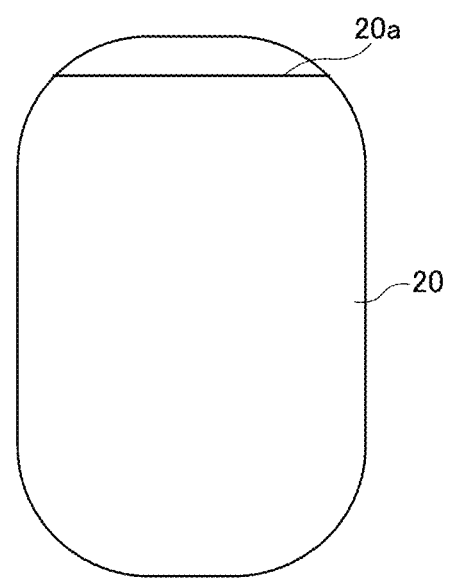
FIG. 3 is a plan view illustrating a lower case forming the deep-body thermometer according to the exemplary embodiment.
Figure 4:
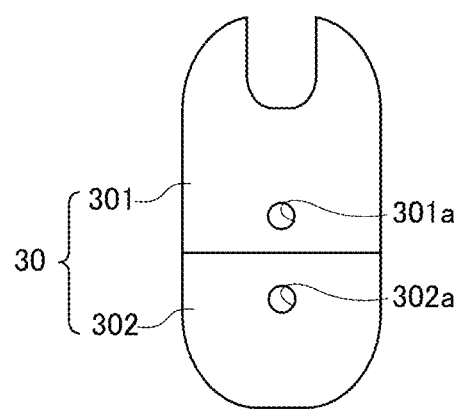
FIG. 4 is a plan view illustrating a thermal resistor layer forming the deep-body thermometer according to the exemplary embodiment.
Figure 5:
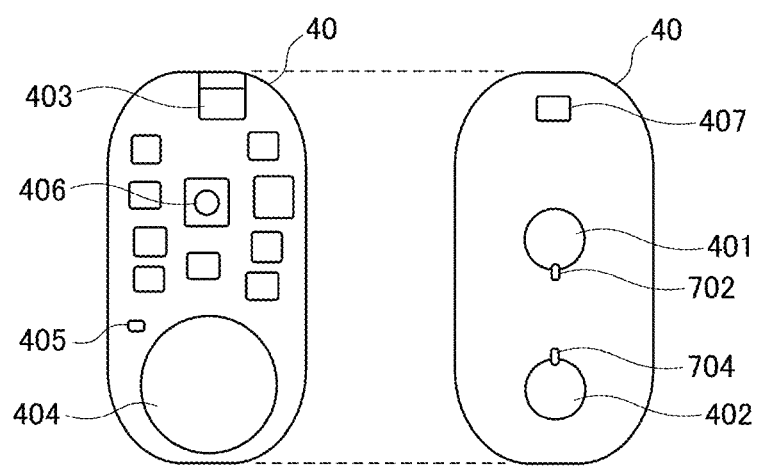
FIG. 5 is a plan view and a bottom view illustrating a wiring substrate forming the deep-body thermometer according to the exemplary embodiment.
Figure 6:
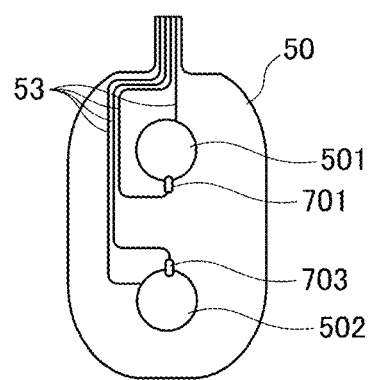
FIG. 6 is a plan view illustrating a flexible substrate forming the deep-body thermometer according to the exemplary embodiment.
Figure 7:
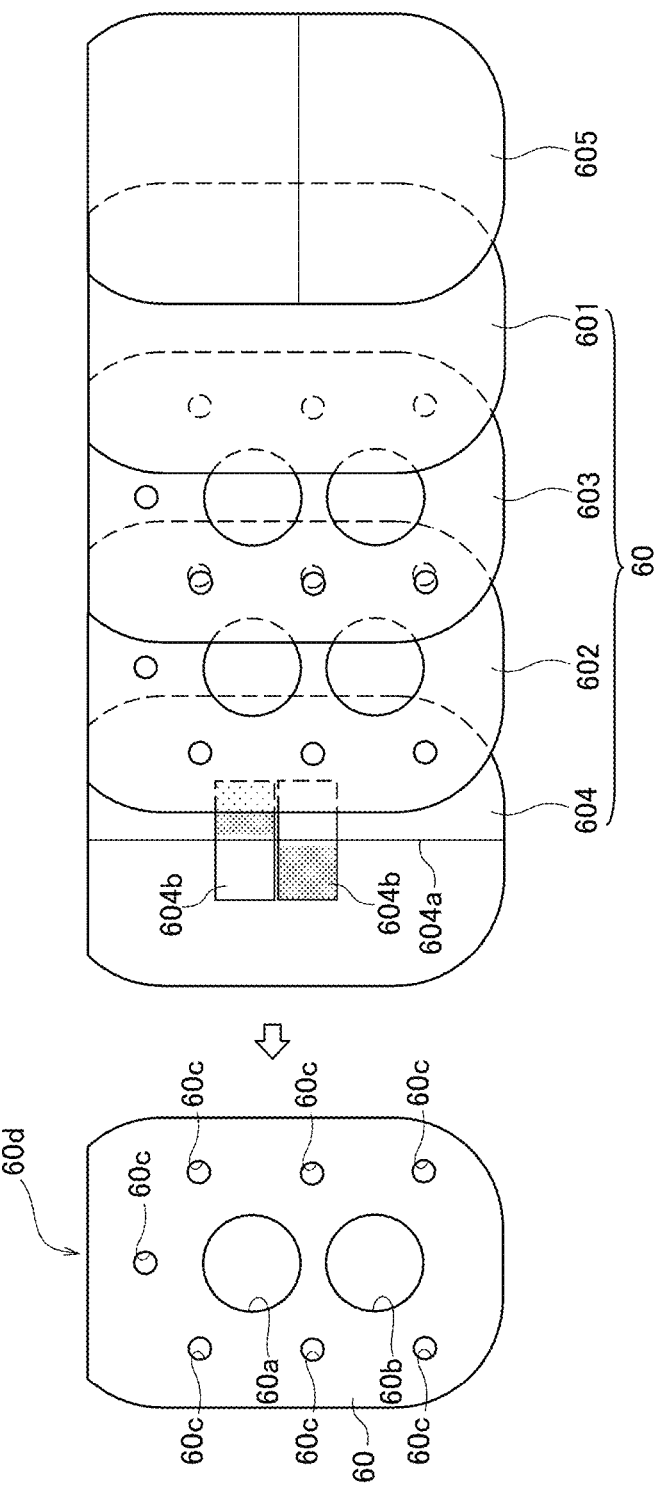
FIG. 7 is a plan view and an exploded view illustrating a sticking member forming the deep-body thermometer according to the exemplary embodiment.

First, a configuration of a sticking type deep-body thermometer 1 according to an embodiment will be described collectively with reference to FIG. 1 to FIG. 7. Here, an exemplary embodiment of a non-heating type deep-body thermometer (hereinafter simply referred to as a "deep-body thermometer") will be described. FIG. 1 is a plan view and a bottom view illustrating an appearance of the deep-body thermometer 1. FIG. 2 is a cross-sectional view (cross-sectional view taken along a line II-II in FIG. 1) illustrating the configuration of the deep-body thermometer 1. FIG. 3 is a plan view illustrating a lower case 20 forming the deep-body thermometer 1. FIG. 4 is a plan view illustrating a thermal resistor layer 30 forming the deep-body thermometer 1. FIG. 5 is a plan view and a bottom view illustrating a wiring substrate 40 forming the deep-body thermometer 1. FIG. 6 is a plan view illustrating a flexible substrate 50 forming the deep-body thermometer 1. FIG. 7 is a plan view and an exploded view illustrating a sticking member 60 forming the deep-body thermometer 1.

According to the exemplary embodiment, the deep-body thermometer 1 is a non-heating type deep-body thermometer in which a heat flow from the deep portion of a target person is obtained based on a temperature difference detected by a first temperature sensor 701 and a second temperature sensor 702, and a temperature difference detected by a third temperature sensor 703 and a fourth temperature sensor 704, and a deep-body temperature is acquired therefrom. Further, the deep-body thermometer 1 is a sticking type deep-body thermometer that is stuck to a body surface of the target person and continuously measures a body temperature to acquire body temperature data. In particular, the deep-body thermometer 1 is a sticking type deep-body thermometer that can be repeatedly used without increasing the cost and without decreasing the measurement accuracy.

The deep-body thermometer 1 is mainly formed of an upper case 10, the lower case 20, a reusable main body portion including a body temperature measurement unit 15, and the replaceable sticking member 60. The body temperature measurement unit 15 is mainly formed of the wiring substrate 40 on which the thermal resistor layer 30, the second temperature sensor 702, and the fourth temperature sensor 704 are mounted, and the flexible substrate 50 on which the first temperature sensor 701, and the third temperature sensor 703 are mounted. Hereinafter, each element will be described in detail.

The upper case 10 is formed of, for example, a closed cell or semi-closed cell foamed material having waterproof property. It is preferable that the upper case 10 use a foamed material with low thermal conductivity in order to prevent the temperature of the body temperature measurement unit 15 from locally changing due to a rapid change in the outside air temperature. As the material, for example, polyurethane, polystyrene, polyolefin, or the like is preferably used. Further, as a processing method of the upper case 10, for example, vacuum molding is preferably used. Moreover, the upper case 10 is formed in a recessed shape in the cross section so that the body temperature measurement unit 15 is accommodated therein. Therefore, a side surface of the thermal resistor layer 30 is covered with the foamed material, and the side surface of the thermal resistor layer 30 is prevented from being exposed to the outside air.

The lower case 20 is formed of, for example, a non-foaming resin film having low water permeability, that is, having waterproof property, and having higher thermal conductivity than the upper case 10. Examples of the material include polypropylene, polyethylene, polyester, and polyimide, and in particular, polyethylene terephthalate is preferably used. The lower case 20 is formed in a planar shape so that the flexible substrate 50, to which the first temperature sensor 701 and the third temperature sensor 703 are mounted, may be fixed in close contact. It is noted that, when a gap is formed between the body temperature measurement unit 15 and the lower case 20, the thermal resistance changes and a heat flux is affected. Therefore, the body temperature measurement unit 15 and the lower case 20 are preferably fixed in close contact with each other using a method to stick to each other by a double-sided tape, a method to fix by an adhesive, or the like. The outer dimensions of the upper case 10 and the lower case 20 are formed to be the same as or substantially the same as each other and are formed to have a size of, for example, about 40 to 100 mm in length and 20 to 60 mm in width.

Then, a peripheral edge portion of the upper case 10 whose cross-section is formed as a recessed shape (e.g., approximately hat-shaped) and a peripheral edge portion of the lower case 20 whose cross-section is formed as a planar shape are fixed in close contact with each other by, for example, sticking with a double-sided tape, fixing with an adhesive, heat sealing or the like. In order to achieve waterproof performance, the portion fixing the upper case 10 and the lower case 20 in close contact are preferably flat and have a structure hard to crinkle. That is, it is preferable that an outer edge portion of the lower case 20 be flat, an outer edge portion of the upper case 10 facing thereto be flat, and these outer edge portions be stuck to each other and fixed in close contact. With this configuration, since the force is uniformly applied to the fixed portion in close contact, the problem causing a bad effect on the waterproof performance, such as a crinkle, is less likely to occur.

As illustrated in FIG. 2, the body temperature measurement unit 15 is formed of the flexible substrate 50, the thermal resistor layer 30, and the wiring substrate 40 laminated in this order from the lower case 20 side.

The thermal resistor layer 30 includes two thermal resistors having different thermal resistance values, that is, a first thermal resistor 301 and a second thermal resistor 302 in order to form two heat fluxes (see FIG. 4). As the first thermal resistor 301, a material having higher thermal conductivity (i.e., a lower thermal resistance value) than that of the second thermal resistor 302, for example, a kind of plastic such as polypropylene, polyethylene, acrylic, polycarbonate, epoxy resin or the like is preferably used. As the second thermal resistor 302, a material having lower thermal conductivity than that of the first thermal resistor 301, that is, a material having a high thermal resistance value, for example, foamed plastic (e.g., foam material) such as polyurethane, polystyrene, polyolefin or the like are preferably used. It is noted that, it is possible to use plastics that are not foamed, rubber, or the like. Here, whereas the thermal conductivity of a metal such as copper, aluminum or the like is 100 [W/m/K] or more, the thermal conductivity of the kind of plastic such as polypropylene, polyethylene, acrylic, polycarbonate, epoxy resin or the like is about 0.1 to 0.5 [W/m/K], and is about three orders of magnitude smaller. The thermal conductivity of the foamed plastic is further almost one order of magnitude smaller. The thermal conductivity of the air is still smaller and is 0.024 [W/m/K]. The first thermal resistor 301 and the second thermal resistor 302 are formed to have substantially the same thickness in order to achieve reduction in cost by allowing laminating with the wiring substrate 40 and the flexible substrate 50.

In the first thermal resistor 301 forming the thermal resistor layer 30, a first through-hole 301a penetrating in a thickness direction is formed. Similarly, in the second thermal resistor 302 forming the thermal resistor layer 30, a second through-hole 302a penetrating in the thickness direction is formed. The first through-hole 301a is formed such that the first temperature sensor 701 and the second temperature sensor 702 are accommodated inside when viewed in a plan view. That is, in the first through-hole 301a, the first temperature sensor 701 and the second temperature sensor 702, which are paired with each other, are disposed along the thickness direction of the first thermal resistor 301. Similarly, the second through-hole 302a is formed such that the third temperature sensor 703 and the fourth temperature sensor 704 are accommodated inside when viewed in a plan view. That is, in (inside) the second through-hole 302a, the third temperature sensor 703 and the fourth temperature sensor 704, which are paired with each other, are disposed along the thickness direction of the second thermal resistor 302.

Here, as the first temperature sensor 701 to the fourth temperature sensor 704 (hereinafter, collectively referred to as "temperature sensor 70"), for example, a thermistor, a temperature measurement resistor, or the like whose resistance value varies depending on a temperature is suitably used. It is preferable that the temperature sensor 70 have as small thermal capacity as possible from the viewpoint of improving response. Therefore, as the temperature sensor 70, for example, a chip thermistor is preferably used. Each of the first temperature sensor 701 to the fourth temperature sensor 704 is electrically connected to a processing circuit, which will be described later, via a printed wiring, and an electric signal corresponding to the temperature is read by the processing circuit.

Incidentally, in order to reduce the size of the heat flow type deep-body thermometer 1, it is important to make the thermal resistor layer 30 (first thermal resistor 301 and second thermal resistor 302) be small. However, when the thermal resistor layer 30 is made to be small, a difference in output values of the paired temperature sensors 70 becomes small, and thus there is a risk that the measurement error may be increased. Here, since the chip thermistor corresponding to the temperature sensor 70 is substantially a rectangular parallelepiped and has a thickness, the thickness of the temperature sensor 70 may not be ignored when the thermal resistor layer 30 becomes thin. When the temperature sensor 70 is in contact with a side surface of the thermal resistor layer 30, heat is transferred from the contact point, and thus there is a risk that the temperature detected by the temperature sensor 70 may become a value deviated from the surface temperature of the thermal resistor layer 30. Therefore, the through-holes 301a and 302a are formed in the thermal resistor layer 30 around the temperature sensor 70, and established is a structure in which the temperature sensor 70 is not in contact with the side surface of the thermal resistor layer 30.

The wiring substrate 40 is, for example, a rigid substrate, such as a glass epoxy substrate, for example. On the wiring substrate 40, a processing circuit is mounted and configured for processing each of output signals of the first temperature sensor 701 to the fourth temperature sensor 704 to acquire deep-body temperature data. In addition, on the wiring substrate 40, a wireless communication unit 403 is mounted that is configured to transmit the acquired deep-body temperature data, and a coin battery 404 that supplies electric power to the processing circuit and the wireless communication unit 403. The processing circuit mainly includes a temperature input circuit and an arithmetic processing circuit. The temperature input circuit is configured to include, for example, an amplifier (such as an operational amplifier), an analog/digital converter (A/D converter), and the like, to read a detection signal (output voltage) of the temperature sensor 70. The temperature input circuit amplifies an analog signal outputted from each temperature sensor 70, converts the amplified analog signal into a digital signal, and outputs the digital signal to the arithmetic processing circuit.

The arithmetic processing circuit is configured to calculate the deep-body temperature from the read measurement data. According to an exemplary aspect, the arithmetic processing circuit can include, for example, a micro control unit (MCU), an EEPROM, a RAM, and/or the like, and is configured to calculate the deep-body temperature based on the detected value of each temperature sensor 70 read via the temperature input circuit. The arithmetic processing circuit stores the calculated deep-body temperature data in a memory such as a RAM. Further, the arithmetic processing circuit is configured to output the calculated deep-body temperature data to the wireless communication unit 403, whereby the calculated deep-body temperature data is outputted to the external device by wireless.

It is noted that, here, in the arithmetic processing circuit, the deep-body temperature is calculated (e.g., estimated) based on the temperature difference between the front and back of the thermal resistors 301 and 302 generated by a difference between two heat fluxes formed by using two thermal resistors 301 and 302 with different thermal resistance. More specifically, the arithmetic processing circuit calculates the deep-body temperature Tb based on, for example, the following equation (1):

$$Tb=\{T1(T3-T4)*Ra1-T3(T1-T2)*Ra2\}/\{(T3-T4)*Ra1-(T1-T2)*Ra2\}$$

Tb represents the deep-body temperature, T1 represents the temperature detected by the first temperature sensor 701, T2 represents the temperature detected by the second temperature sensor 702, and Ra1 represents the heat resistance value of the first thermal resistor 301, respectively. Further, T3 represents the temperature detected by the third temperature sensor 703, T4 represents the temperature detected by the fourth temperature sensor 704, and Ra2 represents the thermal resistance value of the second thermal resistor 302, respectively.

Here, since Ra1 and Ra2 are known, it is possible to uniquely obtain the deep-body temperature Tb by detecting four temperatures (T1, T2, T3, and T4).

On a lower surface of the wiring substrate 40, mounted are the second temperature sensor 702 for detecting a temperature of an upper surface (e.g., outside air side) of the first thermal resistor 301, and the fourth temperature sensor 704 for detecting a temperature of an upper surface of the second thermal resistor 302. More specifically, on the lower surface of the wiring substrate 40, a pair of heat uniforming patterns 401 and 402 for uniforming the temperature distribution of the surroundings are formed. One electrode of the second temperature sensor 702 is connected to the heat uniforming pattern 401, and one electrode of the fourth temperature sensor 704 is connected to the heat uniforming pattern 402. The heat uniforming pattern 401 and 402 are formed of, for example, a material having high thermal conductivity, such as a metal film.

In order to prevent only the temperature of part of the wiring substrate 40 from changing due to the influence of the outside air temperature or the like, it is preferable to provide a uniforming member having high thermal conductivity, which thermally uniform an influence of the temperature distribution of the outside air temperature, to the back side (e.g., outside air side) of the wiring layer on which the second temperature sensor 702 and the fourth temperature sensor 704 are mounted. Here, as the uniforming member, a metal foil, a metal thin plate, or the like may be used, but it is desirable to form it as a wiring pattern of an inner layer of the wiring substrate 40, similar to the wiring layer formed in the wiring substrate 40. In this case, the wiring pattern of the inner layer used as the uniforming member may be a ground pattern, but it is preferable that the wiring pattern be an independent pattern that is not connected to an electric circuit and an electric current not flowing therethrough.

In an exemplary aspect, the wireless communication unit 403 is configured to transmit the acquired deep-body temperature data to an external management device or an information terminal (such as a smart phone). Here, the wireless communication unit 403 transmits the deep-body temperature data to the external management device or the information terminal via wireless, for example, Bluetooth® or the like. The thin coin battery 404 supplies electric power to the processing circuit, the wireless communication unit 403, and the like described above. In order to reduce a planar area of the body temperature measurement unit 15 and to prevent the influence of the change in the outside air temperature or the heat generation accompanied by an operation of the wireless communication unit 403, the wireless communication unit 403 and the coin battery 404 are disposed on the side opposite to the temperature sensor 70 with the wiring substrate 40 interposed therebetween.

On an upper surface of the wiring substrate 40, a power supply switch 406, which accepts an ON/OFF operation of the power supply through the upper case 10, is mounted. Also, on the upper surface of the wiring substrate 40, an LED 405 is mounted that lights or blinks in accordance with an operation by a user (for example, a target person, a nurse, or the like) and a measurement state of the body temperature (for example, on/off of the power supply switch 406, measurement start/end, and the like). It is noted that, instead of the LED, for example, a VCSEL or the like may be used. Further, to a lower surface side of the wiring substrate 40, an FPC connector 407 for electrically connecting the flexible substrate 50 is provided.

The flexible substrate 50 is made of, for example, polyimide, polyester, or the like, and has flexibility. On the flexible substrate 50, mounted are the first temperature sensor 701 for detecting a temperature of a body surface side of the first thermal resistor 301, and the third temperature sensor 703 for detecting a temperature of a body surface side of the second thermal resistor 302. More specifically, as illustrated in FIG. 6, on the flexible substrate 50, a pair of heat uniforming patterns 501 and 502 for uniforming the temperature distribution of the surroundings are formed. One terminal of the first temperature sensor 701 is connected to the heat uniforming pattern 501, and one terminal of the third temperature sensor 703 is connected to the heat uniforming pattern 502. The heat uniforming patterns 501 and 502 are formed of, for example, a material having high thermal conductivity such as a metal film. Each of the first temperature sensor 701 and the third temperature sensor 703 is connected to the wiring substrate 40 (i.e., the processing circuit) via the wiring pattern 53 and the FPC connector 407, and the electric signal (voltage value) corresponding to the temperature is read by the processing circuit (temperature input circuit). As described above, to form the heat fluxes, the lower case 20, the flexible substrate 50, the thermal resistor layer 30, and the wiring substrate 40 are fixed in close contact by, for example, a double-sided adhesive tape or a film with adhesiveness on both sides so as not to generate a gap therebetween.

The sticking member 60 is formed as a sheet-like shape and has a pair of sticking surfaces with adhesiveness. One sticking surface of the pair of sticking surfaces is stuck to an outer side surface (i.e., lower surface) of the lower case 20 in a peelable manner. More specifically, as illustrated in FIG. 7, the sticking member 60 is formed of a first sticking layer 601 whose one sticking surface is stuck to the outer side surface of the lower case 20, a ventilation layer 603 having ventilation property whose one surface is stuck to the other sticking surface of the first sticking layer 601, a second sticking layer 602 whose one sticking surface is stuck to the other surface of the ventilation layer 603, and a release film 604 (also referred to as a "release member") which is stuck to the other sticking surface of the second sticking layer 602. That is, the sticking member 60 is formed of the first sticking layer 601, the ventilation layer 603, the second sticking layer 602, and the release film 604 laminated in this order from the lower case 20 side.

In order to make it hard for the sticking member 60 to be broken when the sticking member 60 is peeled off, it is preferable that the first sticking layer 601 be made of a double-sided adhesive tape including a core material 601a formed by a resin film and adhesive layers 601b and 601b formed on both sides of the core material 601a, or a film with adhesiveness on both sides, as enlarged and illustrated in the right side in FIG. 2. Similarly to the first sticking layer 601, it is preferable that the second sticking layer 602 be a double-sided adhesive tape including a core material, or a film with adhesiveness on both sides, but is not essential.

Further, the sticking member 60 is partially cut out in an outer edge portion, in order to make it easy for such as a fingertip, a nail, or the like to catch when the sticking member 60 is peeled off. In an example illustrated in FIG. 7, an upper end portion of the sticking member 60 is cut out with a straight line (that is, a straight line cutout 60d is formed). It is noted that, in the embodiment, outer edge portions of the first sticking layer 601, the ventilation layer 603, and the second sticking layer 602 are cut out into the same shape. However, it is sufficient that at least part of the outer edge portion of the first sticking layer 601 is cut out, and the ventilation layer 603 and the second sticking layer 602 may not be provided with the cutout 60d. In addition, a portion where the cutout 60d is formed may not be the upper end portion of the sticking member 60. Further, a shape of the cutout 60d may not be a straight line.

Here, adhesive strength between the first sticking layer 601 and the outer side surface of the lower case 20, the adhesive strength between the first sticking layer 601 and the ventilation layer 603, and the adhesive strength between the second sticking layer 602 and the ventilation layer 603 are set to be larger than the adhesive strength between the second sticking layer 602 and the body surface. On the other hand, the adhesive strength between the first sticking layer 601 and the lower case 20 is set to be smaller than the adhesive strength between the first sticking layer 601 and the ventilation layer 603 and the adhesive strength between the second sticking layer 602 and the ventilation layer 603. Degree of adhesive strength is set by changing an adhesive area of each layer or an adhesive material to be used, for example.

In a case where the deep-body thermometer 1 is used while being stuck to the body surface, when sweat is left for a long period of time between the body surface and the deep-body thermometer 1, there is a risk that the body surface causes inflammation. Therefore, the ventilation layer 603 for passing water therethrough is provided to the sticking member 60 so that stuffiness caused by the sweat or the like is suppressed. As the ventilation layer 603, non-woven fabric may be suitably used, for example. By using the non-woven fabric as the ventilation layer 603, it is possible to stick the deep-body thermometer 1 to the body surface in close contact along irregularities of the body surface. Further, it is possible to improve wearing feeling of the deep-body thermometer 1. It is noted that cloth of woven fabric or knitted fabric may be used instead of the non-woven fabric. Further, paper, wood, a foamed material of a sponge/open cell, or the like may be used, and plastic, rubber, or a metal structure, in which grooves or holes extending from the center toward the peripheral edge are formed, may be used.

Since the ventilation layer 603 contains air therein, the thermal conductivity is normally low. Therefore, when the ventilation layer 603 is present on the body surface, the body temperature measurement accuracy is affected. Therefore, in order to stably measure the deep-body temperature, the ventilation layer 603 is not disposed in a region overlapping with the first temperature sensor 701 and the third temperature sensor 703 which measure the temperature of the body surface, and heat uniforming patterns 501 and 502 connected thereto.

Here, a case where the non-woven fabric is used as the ventilation layer 603 will be described as an example. As illustrated in FIG. 7, biocompatible double-sided adhesive tapes or films with adhesiveness on both sides (e.g., first sticking layer 601 and second sticking layer 602) are stuck to both sides of the non-woven fabric. In the ventilation layer 603 and the second sticking layer 602, through-holes 60a and 60b, in which the first temperature sensor 701 and the third temperature sensor 703 are accommodated when viewed in a plan view, are formed in the thickness direction. Here, it is preferable that the through-hole be not formed in a double-sided adhesive tape or a film with adhesiveness on both sides which is stuck to the lower case 20. This is because when the through-hole is formed, an area of the first sticking layer 601 decreases, the lower case 20 is less likely to be in close contact with the body surface, and there arises a risk that the measurement accuracy is decreased.

Normally, the double-sided adhesive tape or the film with adhesiveness on both sides (i.e., the second sticking layer 602) has a lower water permeability than the non-woven fabric (i.e., the ventilation layer 603), and therefore, it is preferable to form a plurality of (seven in the example of FIG. 7) through-holes 60c formed in the thickness direction in at least the second sticking layer 602. In this case, for example, it is preferable to arrange the through-holes 60c having a diameter of about 1 to 10 mm at an interval of about 2 to 20 mm. It is noted that, for example, a cut having an intersecting portion (i.e., a cut intersecting in a cross shape) may be formed instead of the through-hole 60c. In that case, it is preferable to arrange cuts with a length of about 1 to 10 mm intersecting with each other at an interval of about 2 to 20 mm.

The sticking member 60 further includes the film-like or sheet-like release film 604 that is stuck to the other sticking surface of the second sticking layer 602 when the deep-body thermometer 1 is not used. Further, the release film 604 is provided with a knob portion 604b at an outer edge portion thereof. More specifically, the release film 604 is divided into a plurality of (e.g., two in the embodiment) portions by a substantially centered cut 604a so that the release film 604 may easily be peeled off from the other sticking surface of the second sticking layer 602, and the knob portion 604b is provided to the cut 604a of each of the plurality of portions. It is also noted that the knob portion 604b may be provided so as to protrude to the outer side relative to the outer edge of the lower case 20 so that the knob portion 604b may more easily be pinched.

Figure 8:
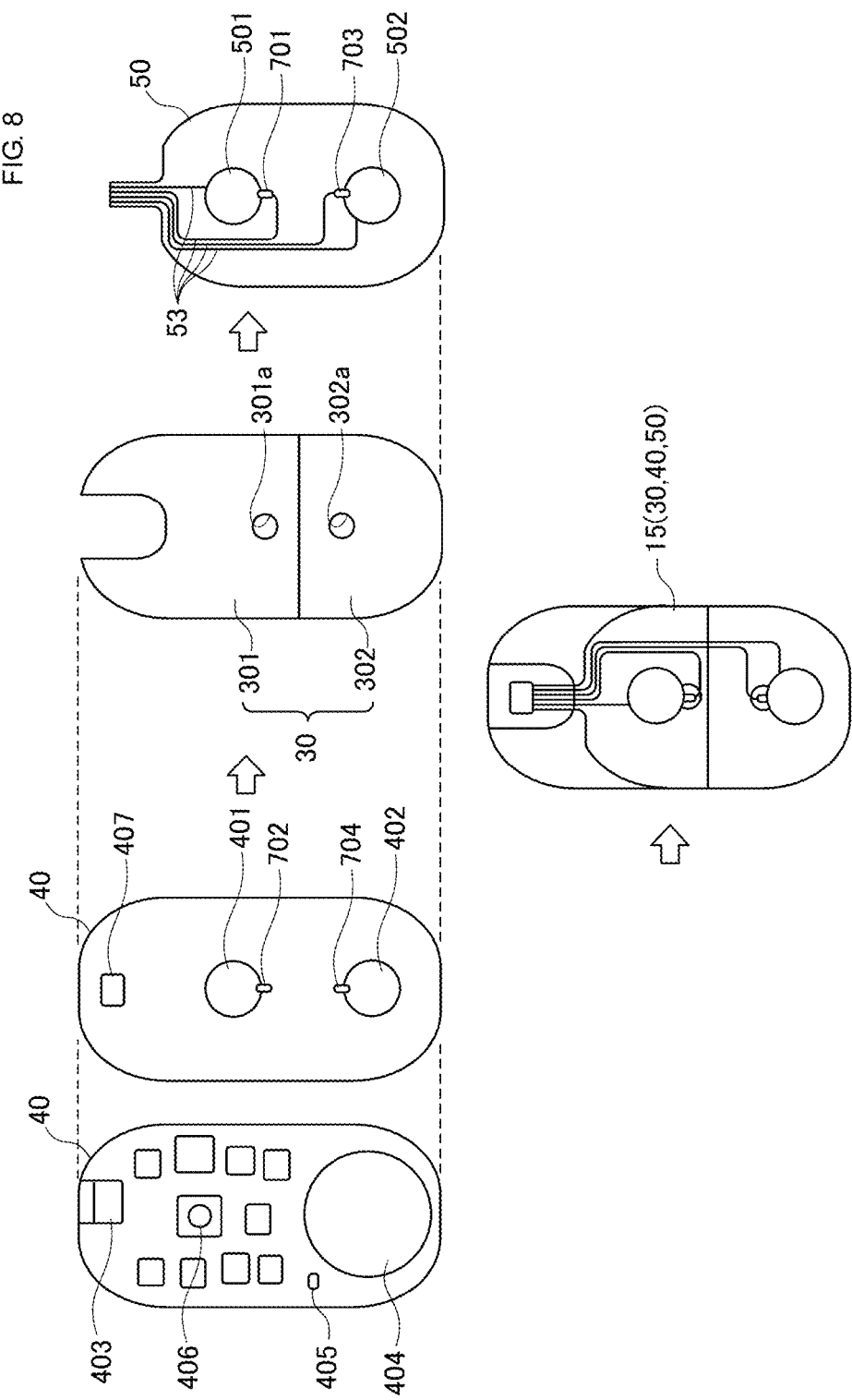
FIG. 8 is a diagram (part 1) for describing an assembling method of the deep-body thermometer according to the exemplary embodiment.
Figure 9:
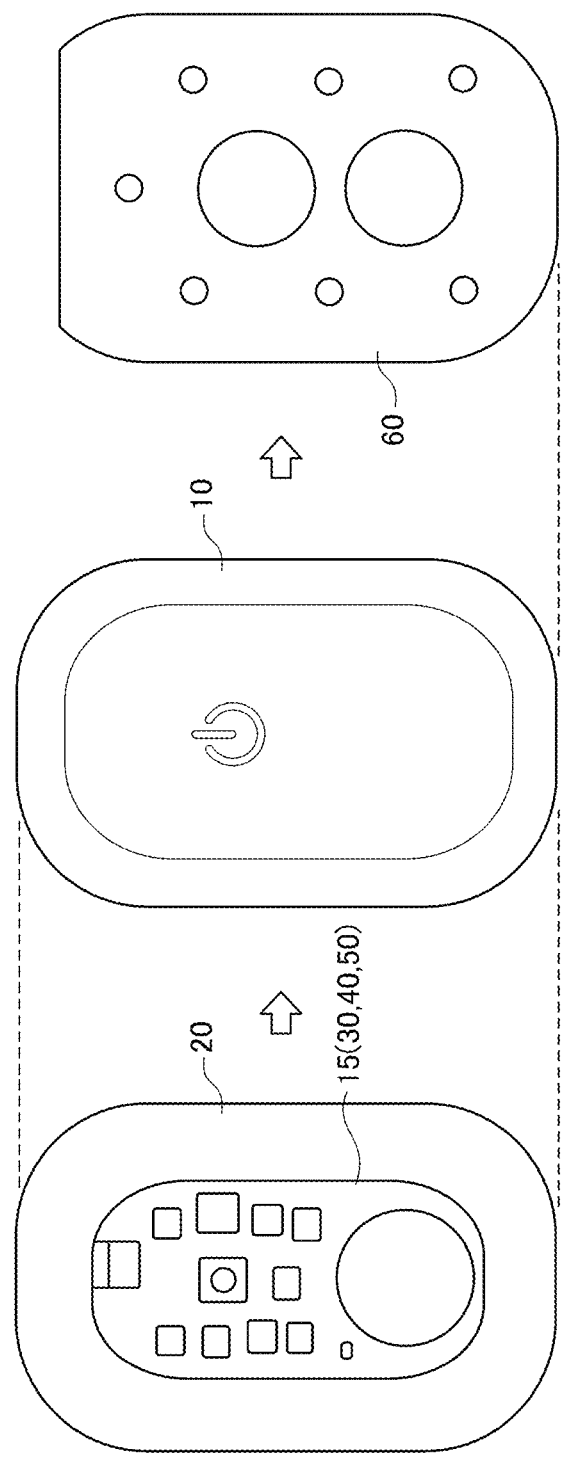
FIG. 9 is a diagram (part 2) for describing an assembling method of the deep-body thermometer according to the exemplary embodiment.

Next, an assembling method (manufacturing method) of the deep-body thermometer 1 will be described with reference to FIG. 8 and FIG. 9 together. FIG. 8 is a diagram (part 1) for describing the assembling method of the deep-body thermometer 1. FIG. 9 is a diagram (part 2) for describing the assembling method of the deep-body thermometer 1.

The deep-body thermometer 1 is assembled, for example, in the following steps (1) to (6).

(1) One surface of the thermal resistor layer 30 (e.g., first thermal resistor 301 and second thermal resistor 302) is fixed in close contact to a back surface of the wiring substrate 40 with a double-sided tape.

(2) After the flexible substrate 50 is connected to the FPC connector 407 of the wiring substrate 40, the flexible substrate 50 is fixed in close contact to the other surface of the thermal resistor layer 30 (first thermal resistor 301 and second thermal resistor 302) with a double-sided adhesive tape or a film 45 with adhesiveness on both sides.

(3) The coin battery 404 is then installed to the wiring substrate 40 (for example, inserted into a battery holder mounted on the wiring substrate 40).

(4) The flexible substrate 50 side of the body temperature measurement unit 15 (i.e., wiring substrate 40, thermal resistor layer 30, and flexible substrate 50) is fixed in close contact to the central portion of the lower case 20 with a double-sided adhesive tape or a film with adhesiveness on both sides.

(5) The peripheral edge portion of the upper case 10 and the peripheral edge portion of the lower case 20 are fixed in close contact with each other with a double-sided adhesive tape or a film with adhesiveness on both sides.

(6) A protection film 605 stuck to the first sticking layer 601 is peeled off, and the sticking member 60 is stuck to the lower case 20 (i.e., the bottom surface). It is noted that, in the embodiment, since the first temperature sensor 701 and the third temperature sensor 703 are not disposed at symmetrical positions with respect to the center of the lower case 20, a mark 20a for indicating a sticking direction of the sticking member 60 is put to the lower case 20. Therefore, when the sticking member 60 is stuck to the lower case 20 such that the mark 20a and the cutout 60d of the sticking member 60 are coincided, a wrong sticking direction is prevented. Note that the mark 20a indicating the sticking direction of the sticking member 60 may be omitted by disposing the first temperature sensor 701 and the third temperature sensor 703 at symmetrical positions with respect to the center of the lower case 20. As described above, the deep-body thermometer 1 is assembled (manufactured).

When the deep-body thermometer 1 assembled as described above is used, first, the knob portion 604b is pinched with fingers, and the release film 604 adhering to the second sticking layer 602 of the sticking member 60 is peeled off from the second sticking layer 602. Then, after the power supply is turned on by pressing the power supply switch 406, the deep-body thermometer 1 is stuck to the body surface of the target person. Since the power supply switch 406 may be erroneously pressed during measurement, for the power supply to be turned on and off, it is preferable to accept an operation by a long press for several seconds or more or multiple times of press, for example. When the operation is accepted, the LED 405 emits light in a predetermined light emission pattern, and notifies the user (for example, a target person, a nurse, or the like) that the operation has been accepted. When the power supply is turned on, the deep-body temperature measurement, the storage of the measurement data in the memory, and the data output by the wireless is started. It is noted that, when the deep-body temperature is measured, a measurement portion is preferably the chest, armpit, back, waist, neck, occiput, or forehead. However, when the body temperature variation is measured, the measurement portion may be the abdomen, flank, thigh, ankle, arm, wrist, or the like.

After the acquisition of the deep-body temperature data is completed, the deep-body thermometer 1 is detached from the body surface of the target person. Then, the sticking member 60 is replaced. That is, the used sticking member 60 is peeled off from the lower case 20, and then the new sticking member 60 is stuck to the lower case 20. Note that, at that time, the protection film 605 stuck to the first sticking layer 601 is peeled off, and the sticking member 60 is stuck to the lower case 20. Note that at this time point (until next use), the release film 604 is left to be stuck.

As described in detail above, according to the embodiment, the sticking member 60 is formed in a sheet-like shape and has a pair of sticking surfaces with adhesiveness, and one sticking surface of the pair of sticking surfaces is stuck to the outer side surface (i.e., the bottom surface) of the lower case 20 in the peelable manner. Therefore, the main body portion composed of the body temperature measurement unit 15, the upper case 10, and the lower case 20 may repeatedly be used by peeling off the used sticking member 60 from the lower case 20 after use (after the body temperature data is acquired), and by sticking the new sticking member 60 to the lower case 20 (i.e., replacing with the new sticking member 60). Further, since the sticking member 60 for sticking the deep-body thermometer 1 to the body surface is replaced, it is possible to prevent a decrease in measurement accuracy due to, for example, a decrease in the adhesive strength, or the like. As the result, it becomes possible to repeatedly use without increasing the cost and without decreasing the measurement accuracy.

According to the embodiment, the sticking member 60 has the first sticking layer 601 whose one sticking surface is stuck to the outer side surface (i.e., the bottom surface) of the lower case 20, the ventilation layer 603 having ventilation property whose one surface is stuck to the other sticking surface of the first sticking layer 601, and the second sticking layer 602 whose one sticking surface is stuck to the other surface of the ventilation layer 603. Therefore, sweat or the like released from the body surface may be discharged to an outside through the ventilation layer 603. Thus, even in a case where the body temperature is continuously measured by sticking the deep-body thermometer (e.g., the sticking type thermometer) 1 for a long period of time, it is possible to suppress the stuffiness of the body surface.

According to the embodiment, since at least part of the outer edge portion of the first sticking layer 601 is cut out, by catching the cutout 60d which is the cut out portion, with a fingertip, a nail, or the like, the sticking member 60 may more easily be peeled off.

According to the embodiment, since the first sticking layer 601 is made of a double-sided tape including the core material 601a formed of a resin film and the adhesive layers 601b and 601b formed on both sides of the core material 601a, the first sticking layer 601 is unlikely to be broken. Therefore, when the sticking member 60 is peeled off, it is possible to pull it with comparatively strong force, and it is possible to more easily peel off the sticking member 60.

According to the embodiment, the adhesive strength between the first sticking layer 601 and the lower case 20, the adhesive strength between the first sticking layer 601 and the ventilation layer 603, and the adhesive strength between the second sticking layer 602 and the ventilation layer 603 are set to be larger than the adhesive strength between the second sticking layer 602 and the body surface. Therefore, it is possible to prevent the sticking member 60 from being left on the body surface side when the deep-body thermometer 1 is detached from the body surface after use.

In addition, according to the embodiment, the adhesive strength between the first sticking layer 601 and the lower case 20 is set to be smaller than the adhesive strength between the first sticking layer 601 and the ventilation layer 603 and the adhesive strength between the second sticking layer 602 and the ventilation layer 603. Therefore, when the used sticking member 60 is peeled off from the lower case 20, it is possible to prevent the first sticking layer 601 or both of the first sticking layer 601 and the ventilation layer 603 from remaining on the side of the lower case 20.

According to the embodiment, since the ventilation layer 603 formed of the non-woven fabric having flexibility is provided between the first sticking layer 601 and the second sticking layer 602, it is possible to stick the deep-body thermometer 1 to the body surface in close contact along the irregularities of the body surface. Therefore, it is possible to improve the measurement accuracy. Further, it is possible to improve the wearing feeling of the deep-body thermometer 1.

According to the embodiment, the release film 604 stuck to the other sticking surface of the second sticking layer 602 is further included, and the knob portion (e.g., tag) 604b is provided (attached) on the outer edge portion of the release film 604. Therefore, when using it (when the body temperature data is acquired), the knob portion 604b is pinched with fingers to peel off the release film 604 from the second sticking layer 602, and the second sticking layer 602 may be stuck to the body surface of the target person. Therefore, the deep-body thermometer 1 may easily be stuck to the body surface of the target person. Further, since the release film 604 is stuck to the other sticking surface of the second sticking layer 602, it is possible to prevent the adhesive strength of the sticking member 60 from decreasing while the deep-body thermometer 1 is not used.

According to the embodiment, the release film 604 is divided into two portions by the cut 604a, and the knob portion 604b is provided in the cut portion 604a of each of the two portions. Therefore, the release film 604 may more easily be peeled off from the second sticking layer 602. Further, when peeling off the release film 604, it is possible to prevent the ventilation layer 603 from causing delamination within the layer.

According to the embodiment, the through-holes 60a and 60b, in which the first temperature sensor 701 and the third temperature sensor 703 are accommodated when viewed in a plan view, are formed in the thickness direction of the ventilation layer 603 and the second sticking layer 602 forming the sticking member 60. Therefore, the deep-body thermometer 1 may be stuck such that the body surface of the target person and the first temperature sensor 701 and the third temperature sensor 703 are in close contact with one another, with the first sticking layer 601 and the lower case 20 interposed therebetween. Thus, since a layer of air with low thermal conductivity is not interposed, it is possible to continuously measure the body temperature with high accuracy and stability. In addition, sweat or the like released from the body surface may be discharged to the outside through the ventilation layer 603. Therefore, even in a case where the body temperature is continuously measured by sticking the deep-body thermometer 1 for a long period of time, it is possible to suppress the stuffiness of the body surface.

According to the embodiment, since the plurality of (e.g., seven) through-holes 60c is further formed in addition to the through-holes 60a and 60b in which the first temperature sensor 701 and the third temperature sensor 703 are accommodated, it is possible to more efficiently discharge the sweat or the like released from the body surface to the outside through the ventilation layer 603. Therefore, even in a case where the body temperature is continuously measured by sticking the deep-body thermometer 1 for a long period of time, it is possible to more effectively suppress the stuffiness of the body surface.

Thus far, the exemplary embodiment of the present invention has been described, but it is noted that it is not limited to the above-described embodiment, and various modifications are possible. For example, a shape, a size, an arrangement of each of the thermal resistor layers 30 (first thermal resistor 301 and second thermal resistor 302), the wiring substrate 40, the flexible substrate 50, the sticking member 60 (first sticking layer 601), second sticking layer 602, ventilation layer 603, and release film 604), and an arrangement of the first temperature sensor 701 to the fourth temperature sensor 704, or the like are not limited to the above-described embodiment, and may be arbitrarily set according to requirements such as accuracy, cost or the like.

In the above embodiment, the case where the present invention is applied to a two heat fluxes type deep-body thermometer has been described as an example, but the present invention may be applied to a one heat flux type deep-body thermometer. In addition, the present invention may also be applied to a thermometer other than a deep-body thermometer. Further, instead of the coin battery 404, for example, a button battery or a secondary battery which is charged with a wireless manner may be used.

Figure 10:
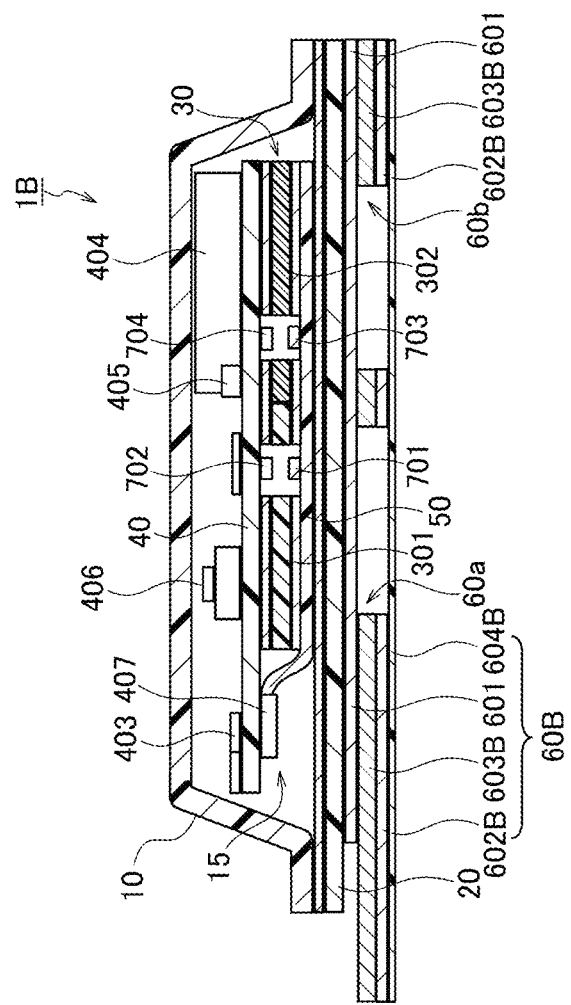
FIG. 10 is a cross-sectional view illustrating a configuration of the deep-body thermometer according to a first modification of an exemplary embodiment.

In the embodiment described above, part of the outer edge portion of the sticking member 60, that is, part of outer edge portion of each of the first sticking layer 601, the ventilation layer 603, and the second sticking layer 602 is cut out in the same shape (e.g., upper end portion in the example illustrated in such as FIG. 7). However, it is sufficient that at least part of the outer edge portion of the first sticking layer 601 is cut out, and as illustrated in FIG. 10, for example, part of the outer edge portion of a ventilation layer 603B and a second sticking layer 602B may be formed to protrude to the outer side relative to the outer edge portion of the lower case 20. Here, FIG. 10 is a cross-sectional view illustrating a configuration of a deep-body thermometer 1B according to a first modification. According to the modification, since part of the outer edge portion of the first sticking layer 601 is cut out and part of the outer edge portion of the ventilation layer 603B and the second sticking layer 602B protrude to the outer side relative to the outer edge portion of the lower case 20, a sticking member 60B may more easily be peeled off by pinching the protruding portion and peeling off.

Figure 11:
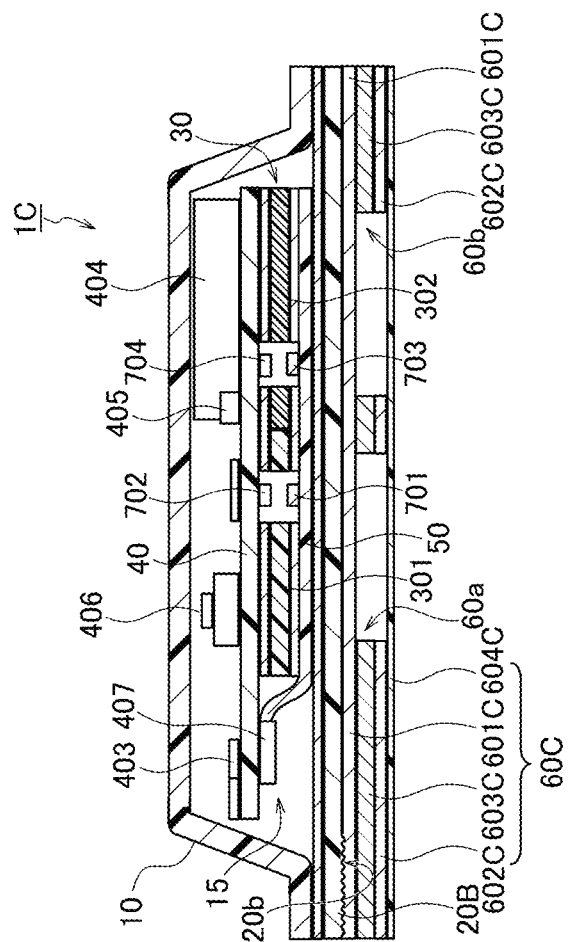
FIG. 11 is a cross-sectional view illustrating a configuration of the deep-body thermometer according to a second modification of an exemplary embodiment.

As illustrated in FIG. 11, part of an outer edge portion of an outer side surface of a lower case 20B may be a rough surface portion 20b whose surface is formed to be rougher than other portions. FIG. 11 is a cross-sectional view illustrating a configuration of a deep-body thermometer 1C according to a second modification. More specifically, in order to reduce the adhesive strength to a sticking member 60C and to facilitate peeling off, part of the outer edge portion of the outer side surface of the lower case 20B is made to be rough by roughening or texturing. However, when the texturing is performed, flatness of the lower case 20B is reduced, and there is a possibility that the waterproof property with respect to the upper case 10 may be affected. Therefore, when the texturing is performed, it is preferable that the texturing do not cross a region in which the upper case 10 and the lower case 20B are stuck to each other. According to the modification, since part of the outer edge portion of the outer side surface of the lower case 20B is formed to be rougher than other portions, the rough surface portion 20b has weaker adhesive strength to the sticking member 60C compared with other portions, and the sticking member 60C is easily peeled off. Therefore, by peeling off the sticking member 60C from the rough surface portion 20b first, the sticking member 60C may more easily be peeled off.

Figure 12:
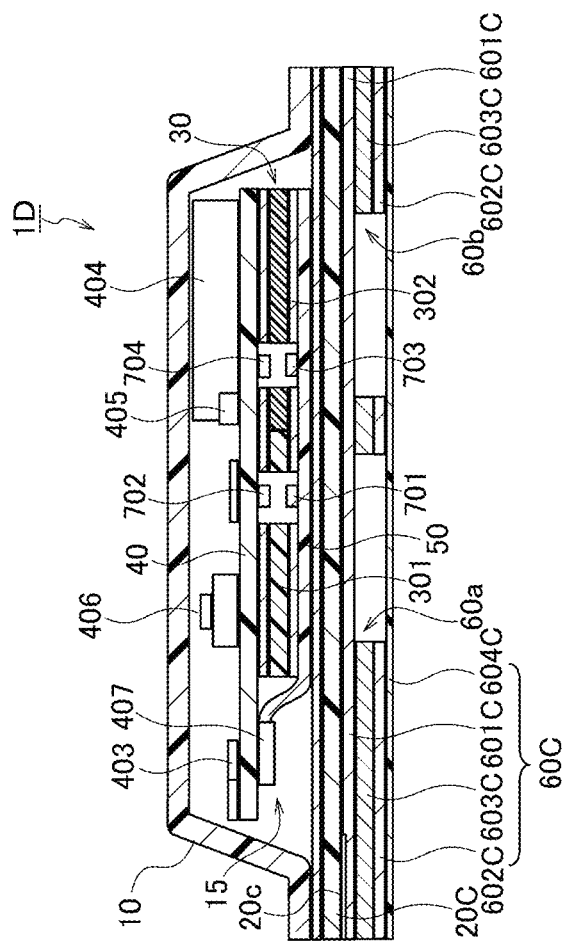
FIG. 12 is a cross-sectional view illustrating a configuration of the deep-body thermometer according to a third modification of an exemplary embodiment.

Instead of roughening the part of the outer edge portion of the outer side surface of the lower case 20B, as illustrated in FIG. 12, a release agent may be coated on part (e.g., end portion) of an outer edge portion of an outer side surface of a lower case 20C. FIG. 12 is a cross-sectional view illustrating a configuration of a deep-body thermometer 1D according to a third modification. In this case, since the release agent is coated on the part of the outer edge portion of the outer side surface of the lower case 20C, a coated portion 20c which is the part of the outer edge portion has weaker adhesive strength with the sticking member 60C compared with other portions, and the sticking member 60C is easily peeled off. Therefore, the sticking member 60C may more easily be peeled off by peeling off the sticking member 60C from the coated portion 20c first.

Figure 13:
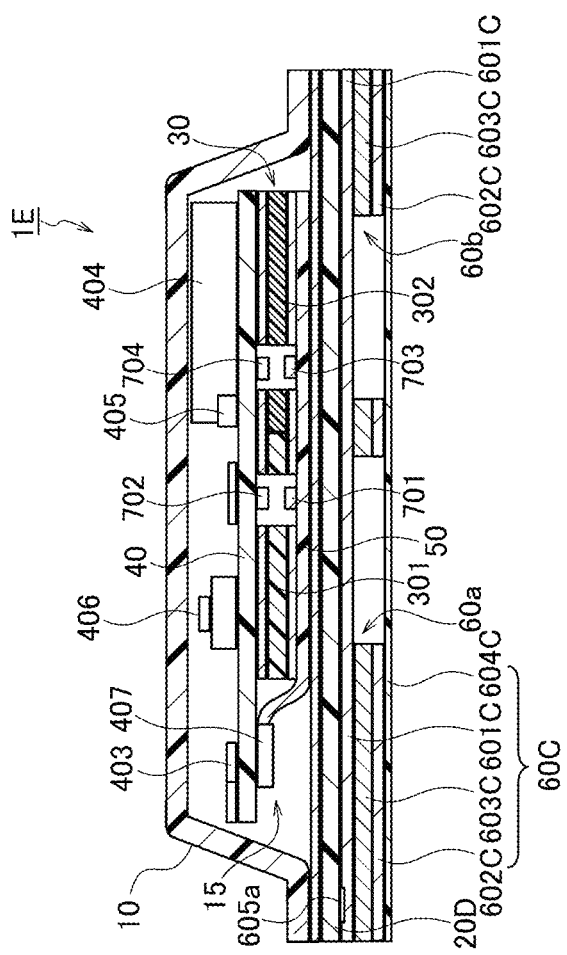
FIG. 13 is a cross-sectional view illustrating a configuration of the deep-body thermometer according to a fourth modification of an exemplary embodiment.

Further, in the above-described embodiment, when the deep-body thermometer 1 is assembled or when the sticking member 60 is replaced, the protection film 605 stuck to the first sticking layer 601 is peeled off and the sticking member 60 is stuck to the lower case 20 in step (6). However, here, by leaving part of the protection film 605 to the first sticking layer 601, a film-like release strip without adhesiveness 605a (corresponding to a residue of a protection film 605B and corresponding to the film-like release strip recited in claims) may be partially sandwiched between one sticking surface of a first sticking layer 601C and an outer side surface of a lower case 20D, as illustrated in FIG. 13. Here, FIG. 13 is a cross-sectional view illustrating a configuration of a deep-body thermometer 1E according to a fourth modification. More specifically, as illustrated in FIG. 14, for example, an elliptical cut is formed in a portion of the protection film 605B, and when the protection film 605B is peeled off, the release strip 605a is left on the first sticking layer 601C. For this reason, it is preferable that the release strip 605a be not peeled off together when the protection film 605B is peeled off, that is, it is preferable that the release strip 605a be in a shape or an arrangement that tends to be left on the first sticking layer 601C side, or only a portion that is left as the release strip 605a be, for example, not subjected to coating treatment or the like of the release agent. According to the modification, since the film-like release strip without adhesiveness 605a is partially sandwiched between the one sticking surface of the first sticking layer 601C and the outer side surface of the lower case 20D, the portion is partially reduced in adhesive strength, and the sticking member 60C may easily be peeled off from the lower case 20D. Note that, here, although a case where the release strip 605a is part of the protection film 605B has been described as an example here, the release strip 605a may be a different piece from the protection film 605B. By doing so, since it is not necessary to perform the coating treatment of the release agent avoiding only a region of the release strip 605a of the protection film 605B and the entire protection film 605B may be subjected to the coating treatment, the coating treatment becomes easy.

Figure 15:
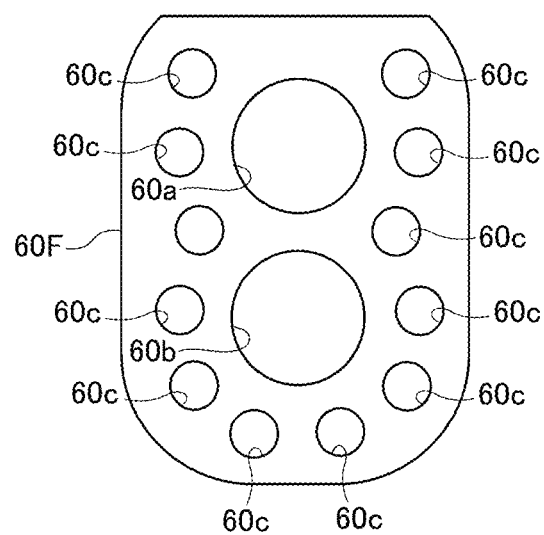
FIG. 15 is a diagram illustrating a sticking member forming the deep-body thermometer according to a fifth modification of an exemplary embodiment.

In the embodiment described above, the plurality of through-holes 60c penetrating through the second sticking layer 602 and the ventilation layer 603 in the thickness direction are formed, and it is preferable that each of the plurality of through-holes 60c formed in the second sticking layer 602 and the ventilation layer 603 be formed as follows. The ratio of the diameter (i.e., diameter when the through-hole 60c has a circular shape) 2r of the through-hole 60c to the thickness D of the second sticking layer 602 and the ventilation layer 603 (i.e., added value of the thickness of the second sticking layer 602 and the thickness of the ventilation layer 603) is larger than 2 (ratio of diameter 2r to thickness D is larger than 2, i.e., ratio of radius r to thickness D is larger 1). In that case, it is preferable that the ratio of the diameter 2r of the through-hole 60c to the thickness D of the second sticking layer 602 and the ventilation layer 603 be set as larger than or equal to 5 and less than or equal to 20 (20≥2r/D≥5, i.e., 10≥r/D≥2.5). Here, FIG. 15 illustrates a configuration of a sticking member 60F forming a deep-body thermometer according to a fifth modification. In the deep-body thermometer according to the fifth modification illustrated in FIG. 15, the ratio of the diameter 2r of the through-hole 60c to the thickness D of a second sticking layer 602F and a ventilation layer 603F is made to be 10 to 15 (15≥2r/D≥10, i.e., 7.5≥r/D≥5).

Figure 16A:
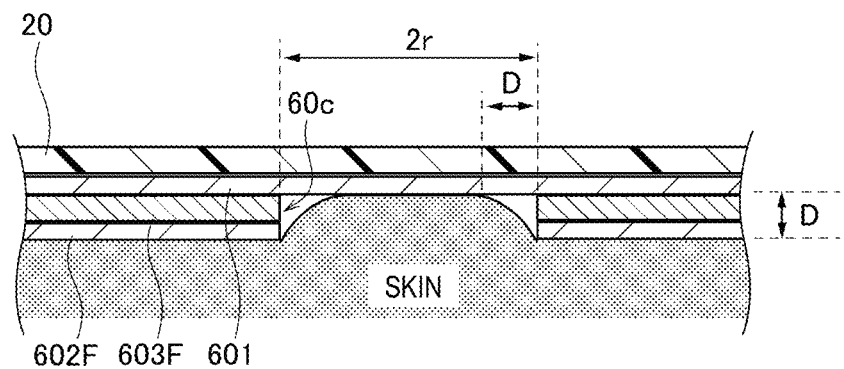
FIGS. 16(a) and 16(b) are diagrams for describing a relationship between a thickness D of a ventilation layer and a second sticking layer, and a radius r of a through-hole and a sticking area of a body surface.
Figure 16B:
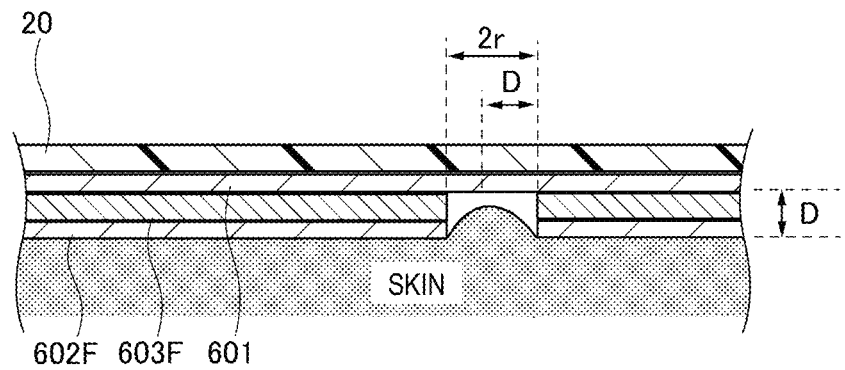

As illustrated in FIG. 16(a) and FIG. 16(b), at a bottom surface of the through-hole 60c (first sticking layer 601), the body surface does not stick to the first sticking layer 601 in a region within substantially the same distance from the circumference of the through-hole 60c in the diameter direction by the thickness D, that is a height of a step of side surface of the through-hole 60c. Therefore, when a ratio of an area of the region described above, that is, the region to which the body surface does not stick increases, to the area of a sticking member 60G, the adhesive strength to the body surface is decreased and there is a risk of peeling off during use. In particular, as illustrated in FIG. 16(b), when the diameter 2r of the through-hole is less than or equal to 2D, there is a high possibility that the body surface does not stick to the first sticking layer 601. On the other hand, as illustrated in FIG. 16(a), when the diameter 2r of the through-hole is larger than 2D, there is a high possibility that the body surface sticks to the first sticking layer 601.

That is, as illustrated in FIG. 17, in the region where the ratio of radius r to thickness D is larger than 1, the larger the radius r of the through-hole 60c is, the larger the area where the body surface sticks to the first sticking layer 601 becomes, and the stronger the sticking strength to the body surface becomes. Note that, FIG. 17 is a graph illustrating the relationship between the ratio of the radius r of the through-hole to the thickness D of the second sticking layer 602F and the ventilation layer 603F (r/D), and the non-sticking area.

Therefore, as described above, in the modification, since the ratio of radius r to the thickness D, which is r/D, is set to be 5 to 7.5, it is possible to more reliably stick the deep-body thermometer. In addition, from a viewpoint of manufacturing, as the diameter 2r of the through-hole 60c becomes large and the number of the through-holes 60c becomes small, it becomes easy to reliably remove residual strips produced during forming of the through-holes 60c, and therefore, it is possible to reduce the manufacturing cost.

Figure 18:
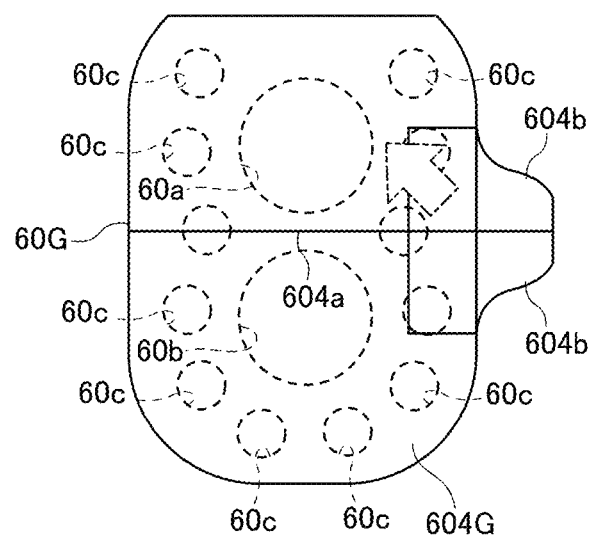
FIG. 18 is a diagram illustrating the sticking member forming the deep-body thermometer according to a sixth modification of the exemplary embodiment.

In addition, in the above-described embodiment, the sticking member 60 is configured as follows. The deep-body thermometer 1 has the film-like or sheet-like release film 604 which is stuck to the other sticking surface of the second sticking layer 602 when the deep-body thermometer 1 is not used (for example, at the time of storage). When the deep-body thermometer 1 is used, the release film 604 stuck to the second sticking layer 602 of the sticking member 60 is peeled off from the second sticking layer 602 by pinching the knob portion 604b with fingers. Here, as illustrated in FIG. 18, a release film 604G with a substantially rectangular shape whose four corners are rounded is divided into a plurality of portions by the cut 604a formed substantially in parallel to a short side of the release film 604G. It is preferable that, in each of the plurality of portions of the release film 604G, the knob portion 604b used for peeling off the release film 604G be provided in a corner portion formed by the cut 604a and a long side of the release film 604G. It is preferable that the knob portion 604b be provided to protrude from the corner portion and to protrude to the outer side of the outer edge of the sticking member 60G so that the intersecting point of the cut 604a and the long side of the release film 604G serves as a point of action of peeling force (i.e., the force applied from the knob portion 604b when peeling off the release film 604G from a second sticking layer 602G by pinching the knob portion 604b), and the peeling force acts from the intersecting point toward an inside of the corner portion. FIG. 18 is a diagram illustrating a configuration of the sticking member 60G forming a deep-body thermometer according to a sixth modification.

More specifically, the knob portion 604b has a first side extended from the cut 604a and a second side intersecting with the long side of the release film 604G, and an angle formed by the long side of the release film 604G and the second side of the knob portion 604b is set to be less than 90°. In particular, the angle formed by the long side of the release film 604G and the second side of the knob portion 604b is preferably 45° or less. As illustrated in FIG. 18, in the modification, the angle formed by the long side of the release film 604G and the second side of the knob portion 604b is set to about 45°. Note that it is preferable that the knob portion 604b provided in one portion divided by the cut 604a, and the knob portion 604b provided in the other portion be formed symmetrically with the cut 604a interposed therebetween.

Incidentally, at the time of peeling off the release film 604G, the non-woven fabric forming a ventilation layer 603G may cause delamination within the layer when the release film 604G is peeled off from the outer edge portion. For example, when the angle formed by the long side of the release film 604G and the knob portion 604b is 90°, the release film 604G is peeled off from the outer edge portion, and the delamination within the layer is likely to occur in the non-woven fabric. On the other hand, as described above, by providing the knob portion 604b at the corner portion and making the angle formed by the knob portion 604b and the outer edge be 45° or less, the force is less likely to act in a direction perpendicular to the outer edge portion, and the release film 604G starts to peel off from the corner portion where the cut 604a and the outer edge portion intersect with each other, so that the release film 604G may easily be peeled off. As the result, the delamination within the layer of the non-woven fabric may be prevented.

Figure 19:
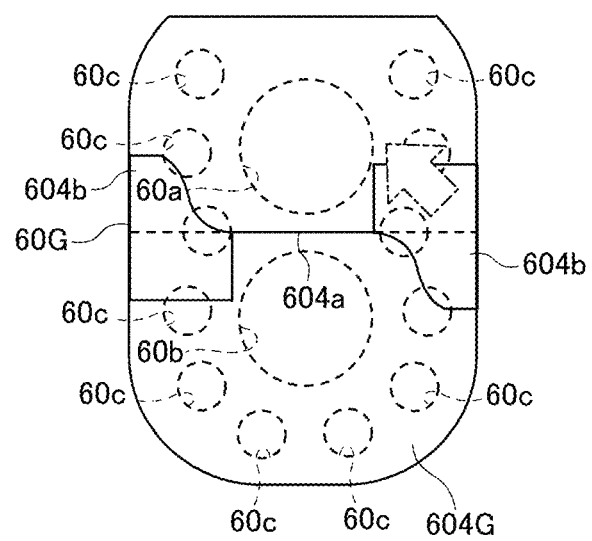
FIG. 19 is a diagram illustrating a first modification of a knob portion of the sticking member forming the deep-body thermometer according to the sixth modification of an exemplary embodiment.
Figure 20:
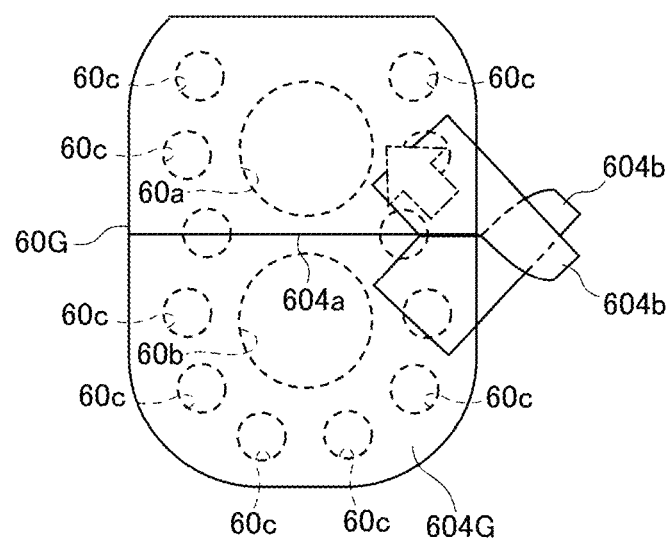
FIG. 20 is a diagram illustrating a second modification of the knob portion of the sticking member forming the deep-body thermometer according to the sixth modification of an exemplary embodiment.

It is noted that, instead of the above-described arrangement of the knob portion 604b, for example, as illustrated in FIG. 19, the knob portion 604b may be provided such that the angle formed by the second side of the knob portion 604b and the outer edge portion may be 0°. It is also noted that, FIG. 19 is a diagram illustrating a first modification of the knob portion 604b of the sticking member 60G forming the deep-body thermometer according to the sixth modification. Similarly, instead of the knob portion 604b described above, for example, as illustrated in FIG. 20, the knob portion 604b may be provided such that the angle formed by the second side of the knob portion 604b and the outer edge portion may be 40°. FIG. 20 is a diagram illustrating the second modification of the knob portion 604b of the sticking member 60G forming the deep-body thermometer according to the sixth modification.

Figure 21:
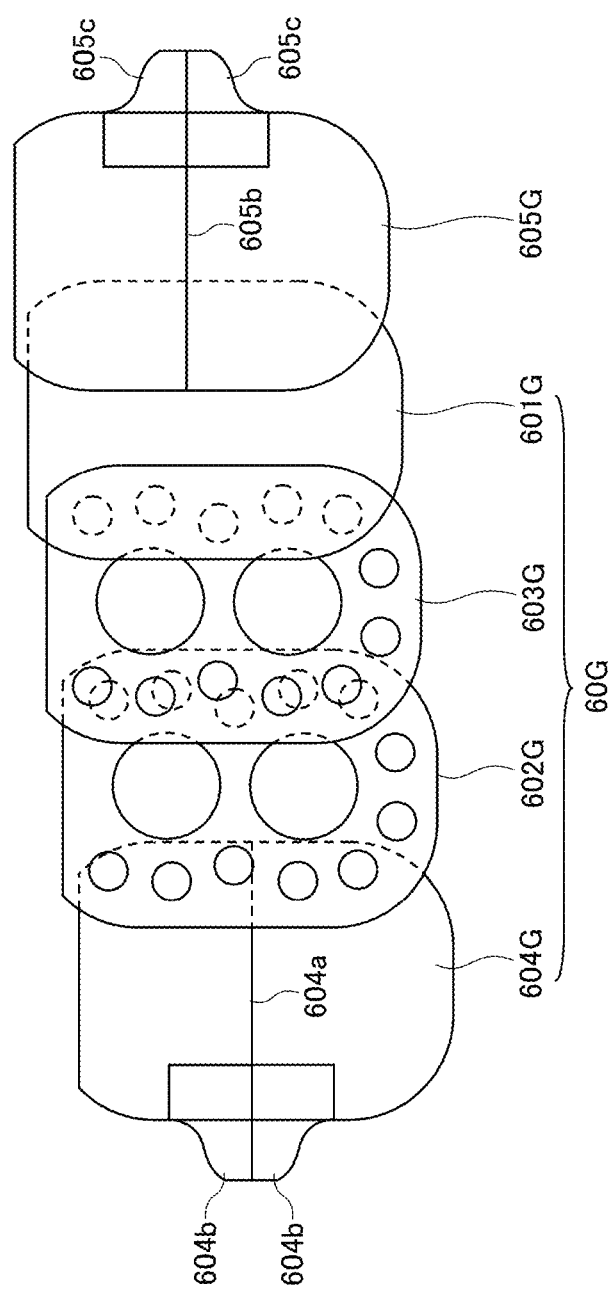
FIG. 21 is an exploded view illustrating a sticking member forming the deep-body thermometer according to the sixth modification of an exemplary embodiment.

Further, in the above-described embodiment, when the deep-body thermometer 1 is assembled, the protection film 605 stuck to the first sticking layer 601 is peeled off, and the sticking member 60 is stuck to the lower case 20 (i.e., the bottom surface). Here, as illustrated in FIG. 21, it is preferable that a knob portion 605c be also provided on a protection film 605G, similar to the release film 604G described above. Note that, FIG. 21 is an exploded view illustrating the sticking member 60G forming the deep-body thermometer according to the sixth modification.

That is, the protection film 605G (e.g., the second release member) is divided into a plurality of (e.g., two in the example of FIG. 21) portions by a cut 605b formed substantially in parallel to the short side of the protection film 605G. In each of the plurality of portions of the protection film 605G, the knob portion 605c which is used when the protection film 605G is peeled off is provided in the corner portion formed by the cut 605b and the long side of the protection film 605G. It is preferable that the knob portion 605c be provided to protrude from the corner portion and to protrude to the outer side relative to the outer edge of the sticking member 60G so that the intersecting point of the cut 605b and the long side of the protection film 605G serves as a point of action of the peeling force, and the peeling force acts from the intersecting point toward the inside of the corner portion. Further, it is preferable that the knob portion 605c have the first side extended from the cut 605b and the second side intersecting with the long side of the protection film 605G, and an angle formed by the long side of the protection film 605G and the second side of the knob portion 605c be less than 90°. In particular, it is preferable that the angle formed by the long side of the protection film 605G and the second side of the knob portion 605c be 45° or less. By providing the knob portion 605c in this manner, the film 605G may easily be peeled off from the first sticking layer 601.

Figure 22:
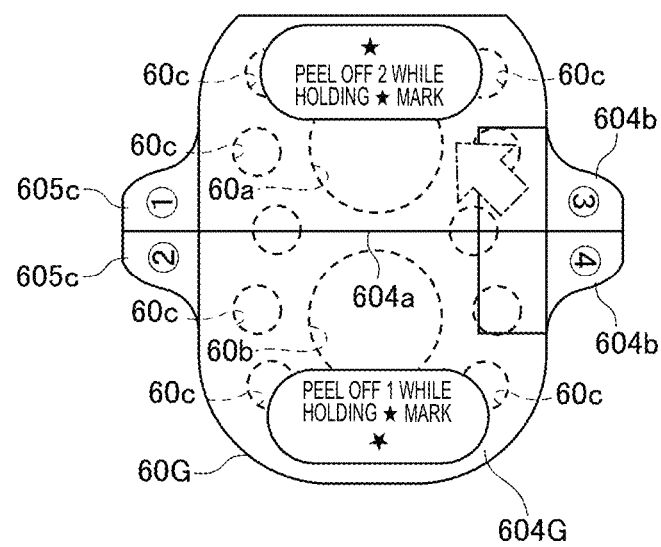
FIG. 22 is a diagram illustrating the sticking member (before sticking) forming the deep-body thermometer according to the sixth modification of an exemplary embodiment.

Further, as illustrated in FIG. 22, it is preferable that the pair of knob portions 604b and the pair of knob portions 605c each have a number of 1 to 4 indicating the order to be peeled off. More specifically, the above-described number is noted so as to be visible from the release film 604G side. In addition, it is preferable that, for example, "★" mark and the phrase (notes) "peel off 1 while holding ★ mark" be noted on the portion of the release film 604G to which one of the knob portions 604b with number 4 is provided (the lower portion in FIG. 22). Similarly, it is preferable that "★" mark and the phrase "peel off 2 while holding ★ mark" be noted on the portion of the release film 604G to which the other knob portion 604b with number 3 is provided (the upper portion in FIG. 22).

When assembling the deep-body thermometer, or when replacing the sticking member 60G, the protection film 605G stuck to the first sticking layer 601 is peeled off, and the sticking member 60G is stuck to the lower case 20. More specifically, first, while holding the "★" mark and the portion noted as "peel off 1 while holding ★ mark" with the fingers of one hand, for example, thumb and index finger of left hand, the divided one side protection film 605G is peeled off by pinching the knob portion 605c of number 1 with the fingers of the other hand, for example, thumb and index finger of right hand. Then, an upper half of the sticking member 60G from which the protection film 605G is peeled off is stuck to the lower case of the deep-body thermometer. Next, in the same manner, while holding the "★" mark and the portion noted as "peel off 2 while holding ★ mark" with the fingers of one hand (for example, thumb and index finger of left hand), the divided other side protection film 605G is peeled off by pinching the knob portion 605c of number 2 with the fingers of the other hand (for example, thumb and index finger of right hand). Then, the entire surface of the sticking member 60G is stuck to the deep-body thermometer.

Then, when the deep-body thermometer is used, the release film 604G sticking to the second sticking layer 602G of the sticking member 60G is peeled off from the second sticking layer 602G by pinching the knob portion 604b of the number 3 with fingers, and the release film 604G sticking to the second sticking layer 602G of the sticking member 60G is peeled off from the second sticking layer 602G by pinching the knob portion 604b of the number 4 with fingers. Then, the deep-body thermometer is stuck to the body surface of the target person. As described above, it is possible to easily and reliably stick (or replace) the sticking member 60G to the deep-body thermometer, and to stick the deep-body thermometer to the body surface of the target person.

REFERENCE SIGNS LIST 1, 1B, 1C, 1D, 1E DEEP-BODY THERMOMETER (STICKING TYPE THERMOMETER)
10 UPPER CASE
15 BODY TEMPERATURE MEASUREMENT UNIT
20, 20B, 20C, 20D LOWER CASE
20b ROUGH SURFACE PORTION
20c COATED PORTION
30 THERMAL RESISTOR LAYER
301 FIRST THERMAL RESISTOR
302 SECOND THERMAL RESISTOR
301a, 302a THROUGH-HOLE
40 WIRING SUBSTRATE
401, 402 HEAT UNIFORMING PATTERN
403 WIRELESS COMMUNICATION UNIT
404 COIN BATTERY
405 LED
406 POWER SUPPLY SWITCH
407 FPC CONNECTOR
50 FLEXIBLE SUBSTRATE
501, 502 HEAT UNIFORMING PATTERN
60, 60B, 60C, 60F, 60G STICKING MEMBER
60a, 60b THROUGH-HOLE
60c THROUGH-HOLE
60d CUTOUT
601, 601C FIRST STICKING LAYER
601a CORE MATERIAL
601b ADHESIVE LAYER
602, 602B, 602C, 602F, 602G SECOND STICKING LAYER
603, 603B, 603C, 603F, 603G VENTILATION LAYER
604, 604B, 604C, 604F, 604G RELEASE FILM
604a, 605b CUT
604b, 605c KNOB PORTION
605, 605B, 605G PROTECTION FILM (RELEASE PAPER)
605a RELEASE STRIP
70 TEMPERATURE SENSOR
701 FIRST TEMPERATURE SENSOR
702 SECOND TEMPERATURE SENSOR
703 THIRD TEMPERATURE SENSOR
704 FOURTH TEMPERATURE SENSOR

The invention claimed is:

1. A thermometer comprising:
a body temperature measurement unit including temperature detector, and a wiring substrate having a processing circuit mounted thereto that is configured to process an output signal of the temperature detector;
an upper case;
a lower case in contact with the upper case to accommodate the body temperature measurement unit therein; and
a sticking member stuck to a surface of the lower case that is facing away from the upper case and includes a double sided tape that includes a core material comprising a resin film and adhesive layers disposed on both sides of the core material,
wherein the sticking member comprises:
a sheet-like shape and has a first sticking layer having a first sticking surface with adhesiveness that is stuck in a peelable manner to the surface of the lower case that is facing away from the upper case,
a ventilation layer having a first surface that is stuck to a second sticking surface of the first sticking layer that is opposite the first sticking surface of the first sticking layer, and
a second sticking layer having a first sticking surface that is stuck to a second surface of the ventilation layer that is opposite the first surface of the ventilation layer.

2. The thermometer according to claim 1, further comprising a film-like release strip that is partially sandwiched between the first sticking surface of the sticking member and the surface of the lower case that is facing away from the upper case, with the film-like release strip being without adhesiveness.

3. The thermometer according to claim 1,
wherein the upper case comprises a hat-like shape having an outer edge,
wherein the lower case includes an outer edge to which the wiring substrate is not fixed, and
wherein the outer edge of the upper case is coupled to the outer edge of the lower case.

4. The thermometer according to claim 1, wherein the upper case is formed of a foamed material, and the lower case is formed of a non-foaming resin film.

5. The thermometer according to claim 4,
wherein the foamed material is selected from a group consisting of polyurethane, polystyrene and polyolefin, and
wherein the non-foaming resin film is selected from a group consisting of polypropylene, polyethylene, polyester, polyimide, and polyethylene terephthalate.

6. The thermometer according to claim 1, wherein at least part of an outer edge of the sticking member is cut out.

7. The thermometer according to claim 1, wherein part of the surface of the lower case that is facing away from the upper case comprises a surface that is rougher than other portions of the lower case.

8. The thermometer according to claim 7, wherein a portion of an outer edge of the surface of the lower case that is facing away from the upper case comprises the surface that is rougher than the other portions of the lower case.

9. The thermometer according to claim 1, wherein a portion of the surface of the lower case that is facing away from the upper case is coated with a release agent.

10. The thermometer according to claim 9, wherein a portion of an outer edge of the surface of the lower case that is facing away from the upper case is coated with the release agent.

11. The thermometer according to claim 1, wherein the ventilation layer comprises a non-woven fabric.

12. The thermometer according to claim 1, wherein an adhesive strength between the first sticking layer and the lower case is less than an adhesive strength between the first sticking layer and the ventilation layer and an adhesive strength between the second sticking layer and the ventilation layer.

13. The thermometer according to claim 12, wherein the adhesive strength between the first sticking layer and the lower case, the adhesive strength between the first sticking layer and the ventilation layer, and the adhesive strength between the second sticking layer and the ventilation layer are larger than an adhesive strength between the second sticking layer and a body surface.

14. The thermometer according to claim 1, further comprising a through-hole disposed in the ventilation layer and the second sticking layer in a thickness direction of the respective layers, with the temperature detector being disposed therein when viewed in a plan view.

15. The thermometer according to claim 14, further comprising a plurality of through-holes having an intersecting portion disposed in a thickness direction of the second sticking layer.

16. The thermometer according to claim 14, further comprising:
a plurality of through-holes disposed in the ventilation layer and the second sticking layer,
wherein a ratio of a diameter of the plurality of through-holes to a thickness of the ventilation layer and the second sticking layer is larger than 2.

17. The thermometer according to claim 1, further comprising:
a film-like release member that is stuck to a second sticking surface of the second sticking layer that is opposite the first sticking surface of the second sticking layer; and
a knob disposed on an outer edge of the film-like release member.

18. The thermometer according to claim 17, wherein the knob protrudes to an outer side relative to an outer edge of the lower case.

19. The thermometer according to claim 17, wherein the film-like release member is divided into a plurality of portions by a cut, and the knob is disposed to the cut portion of each of the plurality of portions.

* * * * *